US011680295B2

(12) United States Patent
Khatib

(10) Patent No.: US 11,680,295 B2
(45) **Date of Patent: *Jun. 20, 2023**

(54) METHODS AND COMPOSITIONS FOR TESTING AND BREEDING CATTLE FOR IMPROVED FERTILITY AND EMBRYONIC SURVIVAL

(71) Applicant: WISCONSIN ALUMNI RESEARCH FOUNDATION, Madison, WI (US)

(72) Inventor: Hasan Khatib, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/345,515

(22) Filed: Nov. 8, 2016

(65) Prior Publication Data

US 2017/0101682 A1 Apr. 13, 2017

Related U.S. Application Data

(63) Continuation of application No. 12/637,753, filed on Dec. 15, 2009, now abandoned.

(60) Provisional application No. 61/122,524, filed on Dec. 15, 2008.

(51) Int. Cl.
*C12Q 1/6883* (2018.01)

(52) U.S. Cl.
CPC ..... *C12Q 1/6883* (2013.01); *C12Q 2600/156* (2013.01); *C12Q 2600/16* (2013.01)

(58) Field of Classification Search
CPC combination set(s) only.
See application file for complete search history.

(56) References Cited

U.S. PATENT DOCUMENTS 8,067,171 B2 * 11/2011 Khatibm .............. C12Q 1/6883 435/6.1

OTHER PUBLICATIONS

Wang (J Dairy Science (2008) vol. 91, pp. 2475-2480).*
Van Wagtendonk-de Leeuw (Theriogenology (2006) vol. 65, pp. 914-925).*
Abraham (Science (1986) vol. 233, pp. 545-548 and alignment).*
BLAST® » blastn suite-2sequences » RID-1MM80ZGW114, https://blast.ncbi.nlm.nih.gov/Blast.cgi, downloaded Dec. 19, 2018.*
Morris ( New Zealand Journal of Agricultural Research (2007) vol. 50, pp. 163-179).*
Gen Bank Accession No. NC_007304.d (Dec. 6, 2006).*
Blast RID-JZ1TE4ZY114 (downloaded Jul. 17, 2019).*
Michael (Endocrinology (2006) vol. 145, pp. 3571-3579).*
Khatib (Journal of animal sciences (2008) vol. 86, pp. 2063-2067).*
Brzokova (Czech J. Anim. Sci., 61, 2016 (8): 377-382).*

* cited by examiner

*Primary Examiner* — Steven Pohnert
(74) *Attorney, Agent, or Firm* — Boyle Fredrickson S.C.

(57) ABSTRACT

Disclosed are arrays of nucleic acid molecules, kits, methods of genotyping and marker assisted bovine breeding methods using SNPs on genes of the bovine interferon tau signaling pathway for improved bovine fertilization rate, or embryo survival, or both.

6 Claims, 10 Drawing Sheets

Specification includes a Sequence Listing.

Coding sequence for Bovine Uterine milk protein (UTMP)

```
1     ggctggattg ccgcagaaat gtcccacggg agaatgaatc tggccctgtc tctggtcttc
61    atcctctgtg gcctgtttaa tagcatcttc tgtgaaaagc aacaacactc tcaaaagcac
121   atgaacctag tcttattaaa gaaaatttca gctctctccc agaagatgga agctcacccct
181   aaggattttg cccaagaatt gttcaaggct ttgataattg aggatcccag aaagaatatc
241   atcttctccc ccatggccat gaccaccacc ctggccaccc tctccctggg gatcaagtct
301   acaatgagaa cccaccaccc tgaggacctg aaacttgagc ccaaactgtt ggatgtgcac
361   aagtacttac agcctctggt ccacgtgggg cgtgagctag tgaagcagaa ggtactgaag
421   caccagcaca ttctctttat caacagaaaa atgatggtca accagatgct tctacagcag
481   ataagcaagc tgcagggaat ggacatccag atgattgact ttacagatat agaaaaagcc
541   aagaagacca tcagccacca tgtggctgaa aaaacacata cgaaaatcac aaacttaatc
601   accgacctga accctgagac catcctgtgt cttgttaacc acattttctt caaaggcatc
661   ttgaaaagag cttttcagcc caaactcacc cagaaggagg tcttctttgt gaatgaccaa
721   accaaagtgc aggtggacat gatgagaaag acagaacgga tgctttacag ccggtcagag
781   gagctacatg ctacgatggt taagatgcct tgcaaaggaa atgtgtccct aactctcatg
841   cttccagatg ccggacaatt tgacactgat cttaaaaaga tgactgctaa gcgagctaaa
901   cttcagaaaa tcagtgactt cagactggtg cgcttaattt tgcccaagtt gaagatctcc
961   ttcaagataa actttaagca tctgcttccc aagattgacc ccaaacatat actgactgcc
1021  acagcaatct cacaggccat cacatcgaag gctcccctgc ctaatttgga ggccctacat
1081  caagctgaga tagagctgag cgagcacgcc ttaaccgtgg acacagccat tcacacagat
1141  aatctgttga aagtcccagt gaaggcaaag gaggtcccgg cggtcgtgaa agtcccaatg
1201  aaggcaaagg aggtcccggc ggtcgtgaaa gtcccaatga acacaaagga ggtcccagtg
1261 gtcgtgaaag tcccaatgaa cacaaaggag gtccc(a/g)gtgg tcgtgaaggt caacagaccc
1321  ttcttgctgt ttgtggagga tgagaagact caaagagacc tctttgtggg caaagtcctc
1381  aacccccaag ttgagtagag ccagggccac actgtgcagc acaggaactt agcaggccat
1441  gaataaaaag agtacaattc acc
```

Notes: The SNP at position 1296 is A/G. A is the nucleotide reported by the original submitter. The SNP is in the coding sequence, but does not change the amino acid sequence of the encoded polypeptide. Primers are designed to be positioned at positions 1071-1090 and positions 1379-1398 (underlined).

FIG. 1

Coding sequence for bovine signal transducer and activator of transcription (STAT1)

```
1     ctttaaatat agcctcaagt ttgccagtgg cttgcctgtg aaatagtgca aagctgtcct
61    gtatctgggc agaggataaa agttatgtgt gttattatat tttccacact ggccattgaa
121   aactaaagat tctctttctt gggagaatta gcttttggta tggctttatg atgctggcta
181 atatcaatag aaggaagtaa actttacaaa tt(c/t)atgagta gtatcttcca tttcagcttt
241   aataccaaag ttgaatatat tctgccttca tcatgaaatt gaagttagta aatgaaactg
301   tcttcacagt tctatcaagg gagccaaact attaacagct ctcttaaggc aaatcctatt
361   attttttcaa aaagttgaaa ttaattgtag atgtaaacaa actcagaaat ttaatgcatg
421   tttcataagt gggttcactt gtctttattg tttagtaaaa attttaaaat tgagaagaaa
481   aactagtaat tgacaaatca ttaggtggag attatgagaa tccaataatt tgaaaactca
541   tcctgtgtaa ctgccttgag aattgggtaa ttttcactgg caaatgtgta tctctcacaa
601   atacattaca gatggttcca ctaaaa
```

Notes: SNP is at position 213 (C/T), with C being the nucleotide reported by the original submitter. Primers are designed to be positioned at positions 11-31 and positions 306-325.

FIG. 2

Partial genomic sequence of the region encoding bovine osteopontin (OPN/SPP1) position 8504

7561 taattaactc taaatattaa aattctcaca attaaagaac aaccactcca aaaaatagcc
7621 accaagcagg ccatttgggc tggttaaatg gatcttccct gcctgttggg cttccctgat
7681 agctcagttg gtaaagcatc tgcctgcaac ttggaagacc cgggttcagt ccctgggtcg
7741 ggaagactcc ctggagaagg aaatggcaac cccctctagt actcttgcct ggaaaatttc
7801 catggactga ggaccctggt aggctaagag tcagacagaa ctgagcaact tcacttcact
7861 ttcctgcctg tttgtaaaag tgagcttagg acaccaattg atctgtcagg ttgtcttccg
7921 gcttaatcct tccacaatga ggctagaaaa ataagacctg ctttggatgg aaacagctaa
7981 cttttgaata aaaaagttac gttgtatgat gtgcactgat ttgtgtcttt tcttcttcag
8041 aattctgtgt cctctgagga aactgatgac aacaaacaaa atgtgagtct ttgctttgat
8101 tctgatgtct gttgtgcctt agactcagga aggcactctt tctcctaatg acattgccca
8161 ggttcaaatt ccggcaaaat tccactagca aacccttcag gaactacttt ttattgggac
8221 tattaatagg gataagttaa atttgctttc cttaagattc tatttgaaga tgctgagaat
8281 ctataagaga agttagataa atgacccagg atatttgcaa atcagaagtg tgatagacat
8341 taactgagct atagtttcta cacatggata agagagtcac cttttgatta tccaggctaa
8401 tagggaggtg attttagttt tggggtgtg cattaataca tggattctct gatcccctga
8461 gaattttcat ttcaaataga aaaggtagtc tcacaattat gta(t/c)ctgtat ttattggatc
8521 attgaaattt ggtaaattag tgtttattat gaacaaggaa aaacagtgtc attgatacaa
8581 atattataac tcatacgttt ggcttgaaa tatctgtgaa aatcgttttt atgagaaacc
8641 aagaaaaatg ccttagaata ggattccatt taccttgtg ttaaaggga aattggaata
8701 agctcatttt agcatttaaa agccattaag tgctttgttg tgaatacaaa gattctaaaa
8761 ctaaataaag atagtaaaat actaatgcac tgtaaagcct aagggacagt aaaaaccctg
8821 acacccattt ttctggccat cttgatttct agaccctccc aagtaagtcc aatgaaagcc
8881 ctgagcaaac agacgatcta gatgacgatg atgataacag ccaggacgtc aactctaatg
8941 actccgacga cgctgaaacc actgatgacc ctgaccattc cgacgagtct caccattctg
9001 atgaatctga tgaagttgat tttcccactg atattccaac aatcgcagtt ttcactccgt
9061 ttatccctac ggaaagcgca aatgatggcc gaggtgatag tgtggcttac ggactgaagt Notes: SNP is at position 8504 (C/T), with T being the nucleotide reported by the original submitter. Primers are designed to be positioned at positions 8316-8338 and positions 8588-8606/7. Positions are numbered according to the GenBank.

FIG. 3

Coding sequence for GHR gene (NC_007318)

```
154261 cagataatga aggataagga aggctggcat gctgcagttc atggggttgc aaagagtcag
154321 acatgactta gcaactgaac agcattctaa aatctgagag tcctagtact gatcttctgt
154381 caaacagtac tttttacgct gtaaaaatgt acaccctgca tatctaagaa gttttaataa
154441 tgattcaaaa atacaacttg gcccccatct tttgatgga tcctcagtct agatcagatc
154501 tagatctaaa gatcacatta aaaaaaaaaa agaattggac attatttagg taaagtagta
154561 tattaacaag catcactttt ccctcaagct aaagcctttt aatgacacac cctgaacaca
154621 taagatgttt aaagcaggtt gtttatataa taaacatgga ttgtgcttaa attgtatgct
154681 gttactcttt ttttttggt atacaaaagg atctgaagaa gtggatagag gtgttcttag
154741 aaaatactaa gtaattgcat tctatttcag tggctatcaa gtgaaatcat tgactttact
154801 agatgaatac aaattaggaa gttttatgtg gaacaggaga atgagatata aacttcaact
154861 gttcatagtt ctgtgagata ttatttttgt gtttttcaga tttccagttt ccatggttct
154921 taattattat ctttggaata cttgggctag cagtgacatt at(t/a)tttactc atattttcta
154981 aacagcaaag gtaagtgtga tataacctac tctgatatgt tttgccagtt atttagcaaa
155041 tgtccatgtt tccatttttt gtttgatgtt ttcttttgtg aatcctgagt gaagtgtttc
155101 atcaacccag tgaaacgtta tcgctctaca tttacatctt tgttgtgtcc acagagagac
155161 aacacaggtc tcagttttat ctggaaagtt gcataggatg ttaagagggt gaggctagtg
155221 actacatacc atgtgacatg caccttaaag ttccgcactg atatttattc caggacccag
155281 aggtagcttt gagcaaaaat ttaagtggtg aactaaagct actagataat tcagtctaat
155341 aaaacctttc tttagacttc atatgatacc aatcttaagt aaatttgggt ttatttaaat
155401 tggttggcta cttacagttt ggtattttac cttcttttgt cagagataaa attctaagtt
155461 tgaggacacc atcctgcatc ctcttgcagc cagaaggcag gtttcagtta ttattctgcc
155521 actgttgttt gagttcattt gagtcccttt atctctagga ctccacgttc tcatgggtaa
155581 tttgagggtg gtggattgta tgatgtttaa gtttccctta agctgtaagg accattattc
```

Notes: SNP is at position position 154,963 (exon 8), with A being the nucleotide reported by the original submitter. Positions are numbered according to the GenBank.

FIG. 4

Nucleotide coding sequence of POU1F1

1 gcaaatactg tgatttgaag ctaaccaaat aaactaattt ctattttggc tggagaagag
61 aaaggaatga aagtagaaac actcgctatt acacatagga gagcctatct gaattcgaga
121 tgctccttag aaatagtaaa taaactctga ttcaggcttg tcttcacccg tttttctctc
181 tgcttcggtt acaaaaccaa accctcacca cttctttctc caggtttagt tcttcagcca
241 tccgcaggat ctcctgagag gaaggcttat tctgttctcc aaagtgtctc tccagggcgt
301 ctttagcagc aatactgatt gttgttctcc gtttctattc ttttgtggga atgagttgcc
361 aacctttac ttcgactgat acctttatac ctctgaattc tgagtcttct gcaactctgc
421 ctctgataat gcatcccagt gctgcggagt gcctaccggt ctccaaccac gccaccaacg
481 tgatgtccac agcaacagga cttcattatt ctgttccttt ctgtcattat ggaaaccagt
541 catcgaccta tggcgtgatg gcagggagct taaccc(c/a)ttg tctttataag tttcctgacc
601 acacgttgag tcatggtttt cctcccatgc atcagcctct cctttcagag gaccccactg
661 ccgctgattt caagcaggag ctcaggcgga aaagcaaatt ggttgaagag ccaatagaca
721 tggattctcc agaaatccga gaacttgaaa agtttgccaa tgagtttaaa gtgagaagaa
781 ttaagctagg atacacccag acaaatgttg ggaagctct ggcagctgtg catggctctg
841 aattcagtca aacaactatc tgccgatttg aaaacctgca gctcagcttc aaaaatgcat
901 gcaaactaaa agcaatatta tccaaatggc tggaggaagc cgagcaagta ggagctttat
961 acaatgagaa agttggtgca aatgaaagaa aaaggaaacg gagaacaaca atcagtattg
1021 ctgctaaaga cgcgctggag agacactttg gagaacagaa taagccttcc tctcaggaga
1081 tcctgcggat ggctgaagaa ctaaacctgg agaaagaagt ggtgagggtt tggttttgta
1141 accgaaggca gagagaaaaa cgggtgaaga caagcctaaa tcagagttta tttactattt
1201 ctaaggagca tctcgaatgc agataggctc tcctattgtg taatagcgat tctacttttc
1261 attcctttct cttctcagcc aaaatagaaa ttagttattt ggttagcnnn aaaaatcaca
1321 tcagtaattt ttgncagaag tgtttctttt ctactttaaa aataaataca atttaaatta
1381 tgttgatgaa ntattctcag aaggannnnn tcantgtaca ntttaagcca aagactaata
1441 ggattaaaac aatgattctg tccctttcac tatatctttc cctctatctc tcccnggaat
1501 tc Notes: SNP is at position 577, with C being the nucleotide orginally reported.

FIG. 5

Coding Sequence for FGF2

1 ccggggccgc gccgcggagc gc(G/T)tcggagg ccggggccgg ggcgcggcgg ctccccgcgc
61 ggctccaggg gctcggggac cccgccaggg ccttggtggg gccatggccg ccgggagcat
121 caccacgctg ccagtccctg ccggaggacg gcggcagcgg cgctttcccg ccgggccact
181 tcaaggaccc caagcggctg tactgcaaga acgggggctt cttcctgcgc atccaccccg
241 acggccgagt ggacggggtc cgcgagaaga gcgacccaca cagtgagtgc tccccaggtc
301 ttccccggtg ccgtcttcgt cccctgcggt tctctccccc gcccctgcct tccagcctcc
361 gcgctccttc ttcctcttca ctgtgacccc ggtgggactt gtggtttctc tccgctcggc
421 cctcggcggt ttcgggctca ccactcgccc ccctcctgcc ccgagctgcg gtggcggtag
481 acgctcctcc aggctttgga gtgtgccggc tgctcagcaa agccagtccc ctgggccccg
541 agcccccggc gcccgggctt tgcgggcggc tccctgggcg cagacaacct gtcgcgtcgg
601 gggtgcccgg cggctgagca gaggtgagcg gctcagcgag gtgccgcccg cgccccgagc
661 ctgaagttcc gaccgcttct atgggatgcc cgttgtctcc ggggcaaagc caggagggac
721 cgcagaccaa ctaaaaggtc cttgttggaa agataccttg catcaggttt gaggatcaaa
781 tgagaatttg aagtgcgcag aggactcaat ttactagtct acagttgcat tttctgtaaa
841 aataataatg atgtatctgt ggtaatagca ataagattgg tctgaggcgt tggttgtcaa
901 actaagagtg cataagaatc acctggaagg tgtgtgtgtt gtgtgattca tggctgaacc
961 atctcccaga gtttcagatc gcttaggtct ggagtggggc ctcatttgca tttctaacta
1021 cttcccaggt gatgctgatc tgggagcaca gtttgagaac ccgctggtct agagaaagag
1081 gaaggaaaga ggtataaaat gggctgataa aaatagatga gtttgaagtg agacaaagag
1141 atcagatatt tttaaactgt catcctgtaa gtgtaggtaa aacatgtttt gaaagctgtt
1201 tgttctgcca ttccttccat aatggttttc aggtggaaaa cttgatcctc tttttttttt
261 tttttttttg cccaagttcc gcaagaggcc ttctttacct tgtgatgcta atagtgcgtc
1321 ctttggggct ctccaggtgg tactggtggt aaagatccca cctgccagtg cctgggatgt
1381 aagaggtgtg gattggatcc ctgtgttgga aagatcccct ggagaaggaa atggcacccc
1441 gctccagtat tcttgcctgg agactcccca tggacagagg agcctagtgg gctaccgtcc
1501 ctagggtccc aaagagtcgg acactgaagg aatttagcaa gctctcactc cgggatgaga
1561 cttaggaaga ggagaaaact ctgcagccaa acctagctga caaattcagt aatgggaaat
1621 gtcccttcat aagaattggt ctttattgat ttcaaaatag caacaagcaa aggattcagg
1681 tctgtaactt ttttccggcc tgccataatt aaacaatttt cttaaccact tacattatcc
1741 agtaaaactg aaaagatgct tgtagcccaa tatatcggtt agtgctcttt ctctattttg
1801 gtaactaggt ttcacaaaat tatctttctg tgtggggttt attctgtgct tgtctgccag
1861 ggtagcccag ctgaacacgg caaggtgcac atatgtccca attaattttg ctcttttcta
1921 gtatcacaaa aagtagtttg ttctttgacg agaagacaga actcttcccc cagattaggt
1981 ttatactgga gcttccttta gtacattttc ttccagacat tttatgagtt gcagtatttt
2041 ctttgccttc tcaataccct atttccttta aaacaaaact gtataggggc tgggctttcc
2101 aggtggcgca gtggtaagga atccgcctgc caatatagga gatgcaggag acactcgttc
2161 aatccctgga ttgggtagat cccctggaaa agggaatggc aaccaactcc agtattcttg
2221 cctgggaaat cccatgagtg gaggagcctg gcaggcacag tccaggggt cccagaaaat
2281 cagacgtgac tgagcacaca ggcatgtatg ggagttagta aggataattc tgaattgcat
2341 attacattac cgccctttta aacacaacta ttaacttttt attcccagtt tggggctggg
2401 ccatcattac tgtattctta ttttaacttc atggtctgaa ataggattga tactctccag
2461 gggacatttg gcagtgcctg gagatgtttt cactcatgcc tggaagggtg ctactgtcat
2521 ttgctaagta gaggccaggg atgttacagt gcacaggaca cctccctaat cgctcagcaa
2581 aaaattaaaa atgttctgac cgtaaatgtt aatagtgtta aggctgagaa acccagccaa
2641 cctgataact agctcgtaga cctttaaagg tagagagtag agtactcatc cagacttgtg
2701 gagagcactg atttttaaaa atcaccttgt accaggtggt agactgacaa gaatagaaac
2761 ctgaaaatga tcaatttaaa tgacttttgt ataggccaac ctggacatat gtttaattaa
2821 ggacagtgtt tttttttttt tttcccctga catatcaaag gtgtactgat agttgacaaa
2881 accaggagga gacaggtaag aaatatatag gaaaaacaat gccatatcag tatcctctta
2941 accatatccc ctccattccc ctaaaggagc aaaactgatc ggcaaacgtg gagaaataaa
3001 agctgttaat gcttgctaca gcttcccacc gaattaaggt tcagagatct agacatattt
3061 gaaacattgg aaaatccaag gccccctccc tcaaactcat ttgtccatac acccaaaatc
3121 tatcactgga gatttatccc tttggcatta actctctgtc cagatgtttc taaaatgcaa
3181 atgcagtgtg ctctccgaat ccacagtctc catctgtggt gatgacagcc gacggcccta
3241 caccgttttc cacgagggac ttgagcctcg gcgggtgctg gaaaccctgg acccgggtcc

FIG. 6A

```
3301 tcatgggtac ggggtggagg gtgcctctgg aaggacaagt ggagcagtta cccggtttta
3361 acatttcgtg tgaattaaat tgtatgtgca tgatttcttc cccaaaagct gaccagcagg
3421 gctggagttg aggggggagg ctgtgaagtc ggtggcatga atgtggggca ctggtcaggg
3481 gcaggggaca tggctaggtt ctgaagggac atagggcagg acggtgtggg gctgggcgga
3541 cagcgtttcc agcttcccac ttttgctgga gatcacctgt gtttctcccc gggtttctc
3601 ttgaattgtt ttcacaattg tttcaaaagg cccactttcc tgcacttttc tcacaatcct
3661 gaaataacct gtatttgaca cgagtgtgtt ggtaaaagcg agataaagac agggccagcg
3721 tgggtgccgc acatccacct tccctttggt gtcccacttg cccacgggga tgtgtaacag
3781 aagtatatgc cctgaagtac tgaaaccatg tgaaaacatt cggaagagag cacattttat
3841 cccaggcagc acgttcaaca tgtggtggag tatagtcagg gcaaagtatg ctgcttgtgt
3901 acattttagc attaaattta ttccagatgc ttttattttg gaaaaaacga aggtagttaa
3961 aagtgctaga tcgacctttg ggtcttctcc caggaggtga ccgcctgctt gccacactcc
4021 tctggcttcc ggcctccaga ggacactgag ccttgaagag gctgagggac ctgcccaccc
4081 ccaagtggag cagggctggg atcccgtctg actcccaccc tctgtgccac cgcacatatt
4141 ccatgcagcc ccgtcattaa aaacgaactg ttcaccagct tcatcttgta gaagacgaga
4201 ttgaggtcca caggcggaac tgattgccgg agtttacctg ccgattcttg cccacttgcc
4261 cccttgcgga ctgtccctgc tgttctggct ttttaggctt cctccacttc aaaatattga
4321 catagtcgct ctggggaggt cttatgagtc cacaggttgc ctctggttgt accccctgga
4381 gcaatgaaga aagccacctt ttcttctctt cctttatgtc aatggaactt ttgattgatg
4441 acaccagatt ctccccccctc cacacacata cacctttttt gggtaatatc tggcaagtgg
4501 atcccaccaa tttactttaa taagcatact gtttactcta atgacatttg tgtgcagtaa
4561 acaaatgaag taagaaccca atagctcatt taattgtgga aatcgtgtaa ttggttcagc
4621 aatgaaagga caattcatga gtcatggata ttaccacacc ttaggagcct tttaaaatga
4681 gtttggtgcc aaatgacttc agcctagaac tggcaatatc ctcttgtgac atgccttgag
4741 ggctttcttt gtgtttataa agtggccatc ccataattgg attttgacag aggtatgaaa
4801 agtggattct gagcattatg ttcagactta cgatgtttta aatggatagc tgagattttt
4861 aggtgtaatt tgaaaaaacg ttatagacaa aacaagaatc atcctcaata cattataatt
4921 ataaaattga ctgttcatct acatattgat tctcagaaat tactctcagc gatattgaaa
4981 aaaggcagta taaggtctcg cattattaga attgttattt tctggccaaa agatgcctgt
5041 ggaacaggga ggtaactact catgtgccat tgcctttact tgtttttcaa aacccccctgc
5101 ttgggcccct ttgtcctaca acaaacatct gtaagactgg cctggggtaa ccactctatt
5161 tctgggaatt ggaacaagac aagtcagcac atttggactt gaaccttaac ctcattacca
5221 tatcctctcc aaacaagtat tctcggttct attttgtttt tgagcttgtc attttctgca
5281 ctctgaaacc aggtcttctg cttaacttgt atgttgtcaa gtgtttggct gttgacaaaa
5341 taattcaagt aacaattatc attgtggaat tttcattatg tcactggtgg ctcagctggt
5401 aaagaatctg cctgcaatgc aggagacctg ggtttgaccc ctagatcggg aagatcctct
5461 ggagaaggaa tgactacccg ctgcagtatt cttgcctgga gaaccccatg gacagaggag
5521 cctggtgggt tacagtgcat ggggttgcaa gagtccgaca tgacttagca actaaactgc
5581 caccaccacg tcaatgggaa atgcagttgt ggcaccgtga ttttcagtgt tcccttactg
5641 catccattgc tgctgctgct aagtcacttc agtcgtgtcc gacggcccac caggctcccc
5701 gtccctggga ttctccaggc aagcacactg gagtgggttg ccatttcctt ctccaatgca
5761 tgaaagtgaa aagtgaaagg gaagtcgctc agtcgtgtcc gactctttgt gaccccatgg
5821 tctgcagcct accaggctcc tccatccatg ggattttcca ggcaagagta ctggagtggg
5881 gtgccgttgc cttctctggc atccattgtt gggggtagc tattgctttc tctctctcta
5941 agctaggtta tttatggcca taggaattta ggcagggaat aagggaaaaa tggcaactcc
6001 cagggaactt cacccattga gccatatacc acatagttct tagaaactgg attagtccca
6061 ttctaaattc ctgtgggata tttttagttt gaagaaattt ggagggccta gaggcaacag
6121 atagccaata ttcagttttt aatttatgtc tcatcccagt tgttccctgt cactgttcct
6181 gcatatggtg acttttgagt tgactggtat atccttaata ctcattcatt tacagtaatc
6241 agtaatgtgt gtgtgtgttt gcattttgat tttcttttaa aaaattattt acttggctgc
6301 tctggatctt agttgctgca tgtgaactct tagttgccac aggtggggtc tagttccctg
6361 accaggatcg aacccaggcc cctccgttgg gagtgcagag gcttagtcgc tgggatacca
6421 gagaagtcgc ctgcatttgt attttcaaag ggctacttac tttctcaagt taagttaccc
6481 tctaaattaa attatcccat agaattctaa agtgtaaagt tcacagattt tttaggatat
6541 tgcagagggt ggggagggaa ggttgttttt tttttttccc tgttttgttt tgctttttaa
6601 aggaaatttg tgtagtgtag taatgatctg gctaggattc tgtgagtggg ttattttctc
6661 tgttcatgat ttatgcactt tgagaaaatt tggcatctta aggtagggac catgacttct
```

FIG. 6B 6721 ccatataaat aaacatcata aaaaggcttg taccttttac tctggtaatt ctcactaaaa
6781 gtgagctgct gatgagaaca ttctatgtgg gtaactactc aggggccaca tgctgttcaa
6841 agcctggtca aggtttacag ttctcttggt atagtaacat atacgattag gcacttagcc
6901 ttttaatgaa gataaatata tgtaacaatt atatttggaa aaatgtaatc atatttgaaa
6961 tattaaaaag ctggctatta gcaattttgg tgtagtctat aaaaagatga atcattgctc
7021 aggataatta gttaaaagct ctcattatga attgttttct ttaaaaagca ttaagatatt
7081 taccatgtac tgtgtgatgg aagattcctc aggtatgctg tgcattgttc atttgtcttt
7141 ctgtgaccgg tatcctagaa tcctgtactc tcttctactt catctccttt tctctttcta
7201 actctggatt gtgcttctgg tattctgctt aaatcattct gggccccggc agtcttccag
7261 ttcaatcaca tggacttacc cagtgtgtca ccctatttct gacacttcac actattgtct
7321 gcctctgtct caccagaatt ccttggcaca ttaacccggt ttcctctcac ccttccaacc
7381 gtcttttcct ctggtccctc ctatcttcgg tcttttgctg ttgtatcccc caaggctctg
7441 tttttgcctc tcttcccatc tttctgagta cttgtgatct ttcagcacag atcatttcaa
7501 ctctctctgc ttttctgtct ctgtgttagt atcgtgttcc tgctgcctaa aggatagatg
7561 tactgccgca gcctcaattc atcccacaga agacagaaca tagcatcatt ttctccacct
7621 ggcacccttc ctactgaatt tctgcctgaa atgaaattct tcttctagtc tccaaaacta
7681 gacacctggg attcatccct gcctcagtga cttttcttcg ccctgtctct tggtttcctc
7741 tgtccttttc ttacctatga acagaccctc cagactttcc ctctgaagca tgacctaccg
7801 gctcagtgtt tcagctcttt acgacccaca ctcccctgat gctgccagcg ctctctgcct
7861 tcgtgattgt ctctaaactg gcagaaccat cactattaca gttggctttt ccacttggtg
7921 atccttgttt ttggaaaatc ctttatcaca ccaattcttg tctcacaccc tcctcccact
7981 ctcacttttc cctgaaaaga tcttttacga gccagctcag tggtcttttc ctttgtgaaa
8041 ctttccccta ccttcccagg gagacttggt tgtttctgtc tgtgcttttt tccccatagt
8101 agttgggatg gattgtagac ttaacagttt ttcttgtaat taattgttta catgtctatc
8161 tcctgcactg ggactgcgag ctctgtctac ttaaagaatg tgttttaagt tcagtgtgta
8221 cccaacaaat gagccaagtc ttctgactcc ctctctgatg gccttctgac atccttctcc
8281 tcttagcctt gactcaggcc gtttccctga gctgaagtgc acttagtcct ccttcctgac
8341 cccagtccta ggctttgcgt cagaccctgt ggctttcaca tggccctgta cccgtctgtc
8401 ctctcctgcg ttatcgaaaa attctctcta atagcttgat gtgttttaac ctcctgtccc
8461 tcagttttac tggaactttc tagatggcaa ggattttaaa aaatttaaac attacccagt
8521 agtcctttgc tctcttttct actctgagga ctgagactga ctttaggcac tccagaattc
8581 cctggactca aatgaatgac catgctgagg cccatgaaga ggttcgatgt gtattgttga
8641 atgagctaga actttaaata aataagcata tacacttcag catgaagtgc gcagagcaga
8701 taagttgaac gtagcatcac tgtggttcct tctgtggaca cctttcacat tattcaaagg
8761 aagcaataaa ggtaaaacac aatcatttca ttaggattaa tttttattgt ggaagttttt
8821 cttttcagct aatgaataac atgtcaacat ttctagccaa tttcagaact agctgtaatc
8881 ttttaattaa aaaccataga tctgagagtt catacttgag tcatatttaa tccttaaatc
8941 cctttctttc cctctgtctc tttctctctt tctaaaagct gtgaatcatt ttataaatta
9001 ggattaagaa ctgtctggta ccattgttaa tatccctttt ggctgtgagg aaatggcaca
9061 aataatttca tcctaatatt cattcagatt tatgagccag tattcatcac aacaatctta
9121 aaactcttga aaggatagaa actgtatgac aaagtgagtc atagtctttg tgatgtgatg
9181 tctgcaaggg tgggtgggag agactactga atgaccagtc tcattctgct ttctgagctg
9241 aatcattttg caaatagaaa acaattcata gatttataga tggtcataac ataaatagga
9301 aatggaagag agtaacagag tcaaataata cctctattta aaaaattact ttttgaaaca
9361 taacacttga tgaacagtct ttattttgaa ttagaaatga aattaatcta ctgcctaata
9421 atacatatat tttgatactt gctgtatgtc tttatatatt ttcatttttt cctattggtt
9481 atgtttcttt taaaaaattc tctcatgtaa tttgaccttt atcttcatag ctatttctag
9541 ctttggcttg tttgacaatt gcgtgtgtgt ttgtgtgtgg agaaggaggg gactacttgt
9601 atggaaactt gagagaagaa ggtccctttc ctcttgaaaa ttcttaatag tataatcctg
9661 cattttgcat ggtcggtctc cttttgttac ttttcatctt actagaatta gcaatatgga
9721 gagtctttct ctgagtcaga tttaaccttt aatctttaaa tgtaagattg atttacctta
9781 tttccttatt ttctttgaga caaagtattt gtcaaaacaa ttatatgaaa agtaaactat
9841 tctagtttga gtgtgtttct tgagttttag aactttagga ctcttcttac attcttatat
9901 ttatccatta aactcaacaa tttagtaagg gggatataat acaaataaaa ttgggaagct
9961 aatttttcta actggtttag tagaggacag tagtatatga agaagacata tattacattt
10021 aatacaacgt gttggattaa aaaatagtta cagcaatacc ttcagctgtt acaaggtggg
10081 aaaagtaagg cgcagattat tttggaggga aggtattaaa accatgacgt gttgatggga

FIG. 6C

```
10141 tctgtccagc ctgagccaga caccaaagca ggttccatgg caacttggcc acgtccctgc
10201 gcctttaaag aggaagggcc tattgtttgg ccttcaccaa atgacttcac ctgggatctt
10261 gttatttact gaatgttttt tgaatggatg gatgaaattc ctgagaacat gctctgggcc
10321 agctttatga acagtatgtt taatcttatt gtagtcttat gaaagaagtg ttattttcat
10381 cttacagata gggatagagt ttttgctatt ggcttttcaa accatggtct ctttgtgatt
10441 gtaagtaatt aattgtgtct tccagatttg ttagtgttta gaatacagtt catggccaga
10501 atttcagatg gacggtgtgg cataaatttg aacagaaata gtgattttta aaaatagttt
10561 aaacttccca gagcctttac tgtgctcagc aaagttagtc tctcatcttt tcttctaccc
10621 ctttattgca tcctttttta tttagaaaat atttgtcatg aattaatacg aaacaattct
10681 ttaatatttt agggattgct ttctgaagaa ctcaaagatt tttaaaaggc atatttaaaa
10741 attaagagca ggacataatt aagaataaat accatataag aatgggataa acctcaaaga
10801 tagagtctgt aaagatgcag aataagctaa ggcatgcaga aaatacaaag agaatgatta
10861 aaaggatgtt taaaaagtta gttaggccct ttcaaggaaa tttgagatag gctcactatt
10921 taaggacata gtgtaagatg aaaagaaaaa aatttagaaa aaaaagcaga tggacctggg
10981 cctattttat gttaatgtta atcttcttct ccaagtgaga ttgtcaatca ataattgtct
11041 gagtgtctca ttgagaaaat aaagaccaag gtagacaaag agatacaaag aaagcactta
11101 gccagacaca tctagaaatg tgtttataat gaaactcctc tttccttgaa atcacttgtc
11161 cccttttttt gacccccctgt attttaaaat ataaaatatt taactttgta aatttcttgc
11221 caaccagccc atctcgcaga gtacatttct actcttcatc ccctcagtct tcacatccgt
11281 ctcaggctct gtgttttcag ttctgctgtg tccttcatac tcacgggggt ctctgcattg
11341 ttgccacagc tgctctcgtt cggtccctga ctgttgcaac tgccttctac ctgatcccat
11401 ctgtatcagt ttgctagggc tgccataaca gattaccgta gactgagtgg ctcaaacaac
11461 agaaattgat tttctcatag ttctgtagac tagaagtcca agatacagct gtctgcatgt
11521 ctggtctttc tgcggcctct tcggggtttg cagcagccac cttacacatg gtcacctctc
11581 tgtgcacaca tcctgatctc ttcttcttgt aagggcacca ttcagatttg gttagggccc
11641 actct(A/G)taac agccccattt tgacttaatc cttctttaga ggccccatct ccaaatagta
11701 attttctgag gtactggggc ttcaggcttc agtgtatgaa tttggggtgg gggtacagtt
11761 cagcccacag caccagtgag tcaactggat attgttcctt ggcagagtat ctttccagag
11821 agcagctctg atcttgttat ccctctattt agaaaaactt catggacagt ctagtcccct
11881 ggttcccaca ttgcttacag atgtgggcac tgtagaaagt ctatgagaat
11941 aggaagttac cagcagatga gtgattgtct tatatatcag aaagtgggat aaaggtattt
12001 tctggaaact ctagatagct aggaagcctg atgtaggtcc ttgaaaaaaa tccaagggac
12061 ttgagaatac ggagaaaaga agataacata gaaaatagta aataggctcg
```

Notes: SNP at position 23 (G/T) position 11646 (A/G) (NC_007304)

FIG. 6D

Coding sequence for STAT5A

```
11221 ggctcagcgt ccctcccctc ccgcaggggc agtgacaccc tgagctgtcc tggggaccct
11281 gagggaggca gagagccagg aggagagcgg gacccagcag agcaggaggc ccgggccttc
11341 ttcctcatgg ggcctgaggg ggagagtcgg tctgggagga ggaggccctg cagggctgtt
11401 ctgagagccc agaagggccg gctgagccac cgcccgaccc tcaggagctg gccgagaagc
11461 accagaagac cctgcagctg ctgcggaagc agcagaccat catcctggat gacgagctga
11521 tccagtggaa gcggcggcag cagctggcgg ggaacggagg gccccccgag ggcagcctgg
11581 atgtgctaca gtcctggtac caggggtggg gggcggggag gggcaggcag cagagtggtg
11641 ctgccagctg ctgtttgcgc ccacgtctac atgagcagct ggctccctct gtctgggcgc
11701 gggtcttatc ccaccagtgg tgtgtttggt gctgacaccg gtgtcccttt ctgtgccccc
11761 tcccctggga ggatgctggg gtggggccag gtggcaaagt ggcgctcagg ctggttggac
11821 cccagtcagt gtcgctcctc ctgggtgttt ctctggtttt tttggaaggc agggcatctc
11881 tgctgtgccc agtgcacagg cgaggtggct cgggcaccag gccttcctgg gggtggagct
11941 gggtgtgggc cttgtccccg cctgggcgcc tgccagcttc tggcctggag gacgggggtg
12001 aagcccgtgt ccttcccttg ggccctgggg ctcgggttca ggtgtgagaa gttggcggag
12061 attatctggc agaaccggca gcagatccgc agagccgagc acctctgcca gcagctgccc
12121 atccccggcc ccgtggagga gatgctggct gaggtcaacg ccaccatcac tgacatcatc
12181 tcagccctgg tgac(c/G)aggtg actcctggcc acgccccgct cccatctggt tgccctgggt
12241 tgggggcagc agggtctttg cagatgggga gctctggctt aaatccttca gtttctgcct
12301 cacaccctcc tcccatccct ctccatcccc tgttgctatg gcctcttgct gtcgacctca
12361 cccagtattt ctcgtggaca ctacacgggc atttgtctcc tgcaactcct ttcagctgct
12421 gagttccttt tactgcctcc cttcccgcca gctcccctga ctcacagtgg ccccagggag
12481 ggtggactgt ccgcaaaccc tcccttcacc tgctcagcct ggtgcaaggc agcctcccca
12541 cgtggaaggt ggggccagag tcctgtcccc tgaagtgtct cctgtccctt gtgtctccgc
12601 agcaccttca tcatcgagaa gcagccccct caggtcctga agacccagac caagttcgcg
12661 gccaccgtgc gcctgctggt gggtgggaag ctgaacgtgc acatgaaccc cccccaggtg
12721 aaggccacca tcatcagcga gcagcaggcc aagtcactgc tcaagaacga gaacacccgc
12781 aagtatgctg cccgctcctt catctgccct cccccagctc agcctctgct ctgtagctgg
```

Note: SNP G/C AT POSITION 12195

FIG. 7

METHODS AND COMPOSITIONS FOR TESTING AND BREEDING CATTLE FOR IMPROVED FERTILITY AND EMBRYONIC SURVIVAL

CROSS-REFERENCE TO RELATED APPLICATION

This is a continuation application of U.S. application Ser. No. 12/637,753 filed on Dec. 15, 2009, claiming priority to U.S. Patent Application 61/122,524, filed on Dec. 15, 2008, the entire disclosure of which is incorporated herein by reference.

STATEMENT OF GOVERNMENT INTEREST

This invention was made with government support under 09-CRHF-0-6055 awarded by the USDA/CSREES. The government has certain rights in the invention.

FIELD OF THE INVENTION

The present invention relates to methods of genetic testing of cattle using molecular genetic methods by assaying for the presence of at least one genetic marker which is indicative of fertility or embryonic survival.

BACKGROUND OF THE INVENTION

Dairy cows are significant investments for dairy farmers, and enormous efforts, such as animal breeding and artificial insemination, have been and continue to be invested in ensuring that the animals have high and sustained productivity, and that the milk produced is of high quality. About 50 quantitative trait loci (QTL) affecting milk production traits have been identified (Bagnato et al., 2008; Lipkin et al., 2008). The dairy cattle genome has been significantly restructured over the past 30 years due to intense selection for production traits.

Such restructuring of the dairy cattle genome over the past 30 years due to intense selection for production traits may have resulted in a hitchhiking effect on a large number of loci adversely affecting fertilization rate and embryo survival, leading to dairy cattle genotypes that are suboptimal for reproductive competence (Royal et al., 2000; Lucy, 2001). The decrease in dairy cattle fertility is a worldwide problem and a major cause of economic loss and cow culling in the global dairy herd.

Many reasons account for this reduced reproductive efficiency, but the most important component seems to be a reduction in embryo survival rate from over 80% twenty years ago to less than 50% today. There appears to be an important genetic basis for this decline (Veerkamp and Beerda, 2007); so genetic approaches may help alleviate this problem. As such, there is an urgent need to identify the genetic factors responsible for the decline in embryo survival rate.

Previously the present inventor has demonstrated the effectiveness of the candidate pathway approach in choosing candidate genes affecting milk production traits (Leonard et al., 2005; Cobanoglu et al., 2006; Khatib et al., 2007a,b; Khatib et al., 2008a; Wang et al., 2008). Recently an in vitro fertilization (IVF) experimental system in cattle has been demonstrated that enables the association of single nucleotide polymorphisms (SNPs) in candidate genes with fertilization rate and embryo survival. Using this system, two genes: fibroblast growth factor 2 (FGF2) and signal transducer and activator of transcription 5 (STAT5A) were found to be significantly associated with variation in fertilization and embryo survival rates (Khatib et al., 2008a,b). These two genes were chosen from the interferon-tau (IFNT) and placental lactogen (PL) signal transduction pathway.

Interferon-.tau. (IFNT) is a major product of ovine and bovine conceptuses during the period before the trophoblast makes firm attachment to the uterine wall and begins to form a placenta. Its primary function is in preventing a return to ovarian cyclicity and hence ensuring the pregnancy to continue, although it undoubtedly has other roles in ensuring receptivity of the maternal endometrium.

IFNT is a member of the Type I IFN family, and signals through the Type I IFN receptor and Janus Kinase (JAK)-signal transducer and activator of transcription (STAT) signal transduction pathway (Stewart et al., Endocrinology 142:98-107 (2001)). IFNT activates multiple STATs and has differential effects on IFN-stimulated response element-(ISRE) and .gamma.-activated sequence (GAS) element-driven gene transcription. It is known to induce a number of genes in the ovine uterus including 2',5'-oligoadenylate synthetase (Johnson et al., Biol. Reprod. 64:1392-1399 (2001)), .beta. 2-microglobulin (Vallet et al., J. Endocrinol. 130:R1-4 (1991)), IFN regulatory factor 1 (Spencer et al., 1998), ubiquitin cross-reactive protein (Johnson et al., Biol. Reprod. 62:622-627(2000)), and Mx protein (Charleston and Stewart, Gene 137:327-331(1993); Ott et al., Biol. Reprod. 59:784-794 (1998)). Many of these proteins are known to function in the antiviral response as well as in early pregnancy of ungulates especially ruminant animals (see e.g. U.S. Pat. App. No. 20070009969). The aforementioned data most likely apply to cattle as well.

Identifying additional genetic factors that show association with fertilization rate or embryo survival rate would enable selection or breeding programs that reduce the frequency of deleterious alleles at these loci by marker- or gene-assisted selection, preventing further decline or even improving reproductive status of the global dairy herd.

Furthermore, a plurality of or multiple genes are likely more reliable than a single gene or SNP in predicting high fertility or enhanced embryo survival.

SUMMARY OF THE INVENTION

The present inventor investigated the effects of various genes of the IFNT signaling pathway and discovered that several of these genes comprise SNPs that are correlated with increased fertilization rate, or embryo survival rate, or both, and these SNPs may be used in breeding programs or other cattle testing or selection programs for cattle with improved fertility, more specifically for increased pregnancy rate in cattle. Accordingly, in one embodiment, the present invention provides a collection, or an array, of at least two of isolated polynucleotide molecule species selected from the group consisting of (1) an isolated polynucleotide comprising at least 12 consecutive nucleotides surrounding position of 1296 of SEQ ID NO:1; (2) an isolated polynucleotide comprising at least 12 consecutive nucleotides surrounding position of 213 of SEQ ID NO:2; (3) an isolated polynucleotide comprising at least 12 consecutive nucleotides surrounding position of 8504 of SEQ ID NO:3; (4) an isolated polynucleotide comprising at least 12 consecutive nucleotides surrounding position of 154963 of SEQ ID NO:4; (5) an isolated polynucleotide comprising at least 12 consecutive nucleotides surrounding position of 577 of SEQ ID NO:5; (6) an isolated polynucleotide comprising at least 12 consecutive nucleotides surrounding position of 23 of SEQ ID NO:6; (7) an isolated polynucleotide comprising at least 12 consecutive nucleotides surrounding position of 11646 of SEQ ID NO:6; and (8) an isolated polynucleotide comprising at least 12 consecutive nucleotides surrounding position of 12195 of SEQ ID NO:7. Preferably, the collection comprises at least three, at least four, at least five, at least six, or at least seven species described above. More preferably, the collection comprises all eight species.

In another embodiment, the present invention provides a method for genotyping a bovine cell, comprising obtaining a nucleic acid sample from said cell and determining the identity of the nucleotide of eight SNP positions in the cell, wherein the eight SNP positions are (1) position 1296 of SEQ ID NO:1; (2) position 213 of SEQ ID NO:2; (3) position 8504 of SEQ ID NO:3; (4) position 154963 of SEQ ID NO:4; (5) position 577 of SEQ ID NO:5; (6) position of 23 SEQ ID NO:6; (7) position 11646 of SEQ ID NO:6; and (8) position 12195 of SEQ ID NO:7, the method, comprising (1) determining the identity of a nucleotide at each of the eight SNP positions, and (2) comparing the identity to the nucleotide identity at a corresponding position of in SEQ ID NOs: 1-7, respectively. In preferred embodiments, the method according to the present invention is used to test an adult bovine cell, an embryonic bovine cell, a bovine sperm, a bovine egg, a fertilized bovine egg, or a bovine zygote. In one embodiment, both copies of the respective gene in the cell are genotyped.

In another embodiment, the present invention provides a method for selectively breeding of cattle using a multiple ovulation and embryo transfer procedure (MOET), the method comprising super-ovulating a female animal, collecting eggs from said superovulated female, in vitro fertilizing said eggs from a suitable male animal, implanting said fertilized eggs into other females allowing for an embryo to develop, and genotyping said developing embryo as described above, and terminating pregnancy if said developing embryo does not all have a corresponding desired polymorphic nucleotide as shown in Table 1A.

DESCRIPTION OF THE DRAWINGS

FIG. 1 shows the partial sequence of the UTMP gene (SEQ ID NO:1) where the relevant SNP position is noted.

FIG. 2 shows the partial sequence of the STAT1 gene (SEQ ID NO:2) where the relevant SNP position is noted.

FIG. 3 shows the partial sequence of the OPN gene (SEQ ID NO:3) where the relevant SNP position is noted.

FIG. 4 shows the partial sequence of the GHR gene (SEQ ID NO:4) where the relevant SNP position is noted.

FIG. 5 shows the partial sequence of the POU1F1 gene (SEQ ID NO:5) where the relevant SNP position is noted.

FIG. 6A. 6B, 6D and 6C together show the partial sequence of the FGF2 gene (SEQ ID NO:6) where the two relevant SNP positions at positions 23 and 11646 are noted.

FIG. 7 shows the partial sequence of the STAT5A gene (SEQ ID NO:7) where the relevant SNP position is noted.

DETAILED DESCRIPTION OF THE INVENTION

It has now been found that many genes encoding proteins of the IFNT signaling pathway contain single nucleotide polymorphisms (SNPs), and certain of these alleles correspond to increased fertilization rate, or embryonic survival rate, or both, in dairy cattle, and the beneficial effects of these alleles are additive. Specifically, it has been discovered that SNPs exist in the following genes: growth hormone receptor (GHR), osteopontin (OPN/SPP1), POU1F1, signal transducer and activator of transcription (STAT1), signal transducer and activator of transcription (STAT5A), bovine uterine milk protein (UTMP), and fibroblast growth factor 2 (FGF2).

These SNPs are summarized in the Table 1 below.

TABLE 1A

Gene Names, SNP Locations, and Polymorphisms

| Gene | SNP Position | Originally Reported Nucleotide | Poly-morphic Nucle-otide | Desired Nucle-otide |
|---|---|---|---|---|
| UTMP | 1296 | A | G | A |
| STAT1 | 213 | T | C | C |
| OPN | 8504 | T | C | T |
| GHR | 154,963 | T | A | A |
| POU1F1 | 577 | C | A | A |
| FGF2 SNP23 | 23 | G | T | G |
| FGF2 SNP11646 | 11646 | A | G | G |
| STAT5A | 11195 | C | G | C |

TABLE 1B

Gene Names, Chromosomal Locations, and References

| Gene | Chro-mosome | SNP (location) | Reference |
|---|---|---|---|
| POU class 1 homeobox 1 (PO U1 F1) | 1 | A/C (exon 3) | Huang et al. 2008 |
| Growth hormone receptor (GHR) | 20 | A/T (exon 8) | Blott et al. 2003 |
| Signal transducer and activator 5A (STAT5A) | 19 | C/G (exon 8) | Khatib et al. 2008 |
| Osteopontin (OPN) | 6 | C/T (intron 4) | Leonard et al. 2005 |
| Uterine milk protein (UTMP) | 21 | A/G (exon 4) | Khatib et al. 2007 |
| STAT1 | 2 | C/T (3'UTR) | Cobanoglu et al. 2006 |
| FGF2 SNP23 | 6 | G/T (5'UTR) | Khatib et al. 2008 |
| FGF2 SNP 11646 | 6 | A/G (intron 1) | Khatib et al. 2008 |

Aside from FGF2 SNP23, the SNPs listed in Table 1 above have been previously reported. Specifically, U.S. patent application Ser. No. 11/179,581 discloses UTMP SNP 1296. (see FIG. 1 of the present invention). This same patent application also discloses STAT1 SNP213 (see FIG. 2) and OPN SNP8504 (see FIG. 3).

GHR SNP 154963 was reported by Blott et al. 2003 (Genetics 163:253-266) (see FIG. 4).

U.S. patent application Ser. No. 12/267,104 discloses POU1F1 SNP 577 (see FIG. 5).

U.S. Pat. App. No. 61/046,253, filed on Apr. 18, 2008, discloses FGF2 SNP11646 (see FIG. 6). FIG. 6 further depicts FGF2 SNP23.

U.S. patent application Ser. No. 12/267,076 discloses STAT5A SNP 12195 (See FIG. 7).

These and other references cited herein are all incorporated by reference in their entirety.

POU1F1 is a member of the tissue specific POU (Pit, Oct, Unc) homeobox transcription factor DNA binding protein family that is found in all mammals studied so far (Bastos et al., 2006; Ingraham et al., 1988; Ingraham et al., 1990). The pituitary specific expression of POU1F1 is required for the activation of growth hormone (GH), prolactin (PRL), and thyroid stimulating hormone (TSH) (Li et al., 1990). These genes are involved in a variety of signaling pathways that are important for many developmental and physiological processes, including pituitary gland development (Li et al., 1990. Mullis, 2007), mammary gland development and growth (Svennersten-Sjaunja and Olsson, 2005), milk protein expression (Akers, 2006), and milk production and secretion (Svennersten-Sjaunja and Olsson, 2005). Moreover, binding of GH and PRL to their receptors on the cell membrane triggers a cascade of signaling events including the JAKISTAT pathway, which has been shown to be required for adult mammary gland development and lactogenesis (Liu et al., 1997).

Several genes in the same pathway of POU1F1 have been reported to be associated with different milk production and health traits. For example, growth hormone receptor (GHR) has shown associations with milk yield and composition (Viitala et al., 2006). Also, the signal transducer and activator of transcription 1 (STAT1) and osteopontin (OPN) genes have been shown to have significant effects on milk yield and milk protein and fat yields in Holstein dairy cattle (Cobanoglu et al., 2006; Leonard et al., 2005; Schnabel et al., 2005). The uterine milk protein (UTMP) is another gene in the pathway of POU1F1 that has been found to be associated with productive life in dairy cattle (Khatib et al., 2007b).

The FGF2 regulates the trophectoderm expression of interferon-.tau., a key member of the signal transduction pathway involved in milk production (Ocon-Grove et al., 2007). Bovine FGF2 is mapped to chromosome 17, with 3 exons and a total length of over 55 kb; it is expressed by the endometrium throughout the estrous cycle and early pregnancy (Michael et al., 2006).

The signal transducer and activator (STAT) proteins are known to play an important role in cytokine signaling pathways. STAT proteins are transcription factors that are specifically activated to regulate gene transcription when cells encounter cytokines and growth factors, hence they act as signal transducers in the cytoplasm and transcription activators in the nucleus (Kisseleva et al., 2002). In mammals, STATs comprise a family of seven structurally and functionally related proteins: STAT1, STAT2, STAT3, STAT4, STAT5a and STAT5b, STAT6 (Darnell, 1997). The seven mammalian STAT proteins range in size from 750 to 850 amino acids. The chromosomal distribution of these STATs, as well as the identification of STATs in more primitive eukaryotes, suggest that this family arose from a single primordial gene (Chen et al., 1998). In addition, STATs share a number of structurally and functionally conserved domains.

The STATS protein is also known as the mammary gland factor. This protein was initially identified in the mammary gland as a regulator of milk protein gene expression (Watson, 2001). STAT5A is a member of the interferon-tau (IFN-tau) and placental lactogen (PL) signaling pathway, which is involved in signal transduction within a variety of cells, including the uterus and mammary epithelial cells. The uterus is exposed to IFN-tau and PL, as well as many others hormones including estrogen, progesterone, and placental growth hormone. The PL stimulates the formation of STAT5 homodimers, which in turn induce the transcription of the bovine uterine milk protein (UTMP) and osteopontin (OPN) genes (Spencer and Bazer, 2002; Stewart et al., 2002; Spencer and Bazer, 2004). In previous studies, the present inventor showed that the UTMP (Khatib et al., 2007a) and OPN (Leonard et al. 2005; Khatib et al. 2007b) genes have surprisingly strong effects on milk production and health traits in cattle. Furthermore, the present inventor showed that STAT1—also member of the IFN-tau and PL signal transduction pathway—is associated with milk composition and health traits (Cobanoglu et al., 2006).

Studies in mouse have shown that STAT5A is involved in both milk production and fertility; Stat5 knockout female mice fail to lactate (Miyoshi et al., 2001). Also, it has been shown that disruption of Stat5 leads to infertility in females as a result of small-sized or a lack of corpora lutea (Teglund et al., 1998). Because the primary source of progesterone is the corpora lutea of the ovary, lack of development of corpora lutea would have significant effects on the establishment of pregnancy.

Polymorphisms at the nucleic acid level may provide functional differences in the genetic sequence, through changes in the encoded polypeptide, changes in mRNA stability, binding of transcriptional and translation factors to the DNA or RNA, and the like. Polymorphisms are also used to detect genetic linkage to phenotypic variation.

One type of polymorphism, single nucleotide polymorphisms (SNPs), has gained wide use for the detection of genetic linkage recently. SNPs are generally biallelic systems, that is, there are two alleles that an individual may have for any particular SNP marker. In the instant case, the SNPs are used for determining the genotypes of the POU1F1 gene, which are found to have strong correlation to longevity and milk production traits.

Through the following testing and analysis, it has been established that certain alleles of the SNPs shown in Table 1 correspond to increased fertilization rate, or embryonic survival rate, or both, in dairy cattle, and the beneficial effects of these alleles are additive.

Gene Selection and Genotyping. The genes POU1F1, GHR, STAT5A, OPN, UTMP, STAT1, and FGF2 were chosen for association tests with fertility traits because they are members of the IFNT and PL/POU1F1 pathway. Genotyping of these genes was performed as described in the literature (Table 1) except for GHR, for which primers, GHR-F CTTTGGAATACTTGGGCTAGCAGTGAC A"A"-TAT (SEQ ID NO:8) and GHR-R GTCTCTCTGTGG-ACACAACA (SEQ ID NO:9) were used to amplify a 230-bp genomic fragment. The original T nucleotide at position −4 of the SNP was mutated to an A nucleotide in the forward primer to create an Ssp/recognition site. Restriction enzyme digestions were carried out according to the manufacturer's instructions.

Fertility Data Collection. Ovaries from mature cows were collected from a local abattoir and immediately used in the IVF experiments as described in Khatib et al. (2008a,b). Briefly, oocytes were aspirated from antral follicles (>2-6 mm) and immediately incubated in maturation medium. On average, 12 oocytes were aspirated from each ovary. On day 2 (d 2), oocytes were fertilized with frozen-thawed percoll-separated semen that had been adjusted to a final concentration of 1 million sperm/ml. Fertilization rate was calculated as the number of cleaved embryos at 48 h post fertilization out of total number of oocytes exposed to sperm. Survival rate of embryos was calculated as the number of blastocysts on d 7 of development out of the number of total embryos cultured. Viability was determined as a function of the embryo's ability to attain the morphological stage of blastocyst on d 7 of development. Embryos that failed to show cellular compaction (morula stage) on d 5 or d 6 were considered nonviable. Therefore, only embryos exhibiting adequate compaction followed by the formation of a blastocoele on d 7 were considered viable. Ovaries from which fewer than 4 oocytes were harvested were discarded and not further analyzed. A total of 7,413 fertilizations were performed using oocytes from a total of 504 ovaries and semen from 10 different bulls.

Association of Individual Genes with Fertilization and Survival Rates. Associations of individual genes with fertilization and survival rates were analyzed using the following logistic regression model:

$$\log\left(\frac{p}{1-p}\right)_i = \beta_0 + \beta_{1j} Bull_j + \beta_{2k} Genotype_k \qquad (1)$$

where $$\log\left(\frac{p}{1-p}\right)_i (i = 1, 2, \ldots n)$$

is the natural logarithm of odds of survival rate or fertilization rate, $\beta_0$ is a general constant, $\beta_{ij}$ is the fixed effect associated with the $j^{th}$ bull ($Bull_j$); and $\beta_{2k}$ is the genotype effect associated with the $k^{th}$ genotype ($Genotype_k$) of the gene analyzed. This model was fitted by Maximum Likelihood approach. Association between the gene and survival/fertilization rate was tested using a Likelihood Ratio Test (LRT).

Association of Candidate Genes with Embryonic Survival. The GHR, STAT5A, UTMP, FGF2 SNP11646, FGF2 SNP23, and STAT1 genes showed considerable associations with embryonic survival rate (Table 2). For GHR, the survival rate of embryos produced from AA ovaries was 9% higher than that of embryos produced from TT ovaries. For STAT5A, CC ovaries showed 9% and 8% higher survival rates than that of GG and GC ovaries, respectively. The UTMP gene showed 6% survival rate differences between AA and GG genotypes (Table 2). SNP11646 and SNP23 of FGF2 showed differences of 7% each between genotypes GG and AA and between GG and TT, respectively. For STAT1, although not statistically significant, TT genotype was associated with a 4% increase in survival rate compared to GG genotype.

Association of Individual Genes with Fertilization Rate. The POU1F1, GHR, STAT5A, OPN, STAT1, and FGF2 SNP23 showed association of with fertilization rate (Table 3). The CC genotype of POU1F1 was showed 71.4% fertilization rate vs. 67.7% for AC genotype. Also, AA genotype of GHR showed 70% fertilization rate compared to 66% for AT genotype. Ovaries carrying the TT genotype of OPN showed a 70% fertilization rate vs. a 62% rate for ovaries carrying the CC genotype. The CC genotype of STAT5A showed significant association with fertilization rate (71%) vs. the GC (69%) and GG (66%) genotypes. The genotypes of STAT1 genes (CC vs. TT) showed 3% difference in fertilization rate. Similarly, although less statistically significant, FGF2 SNP23 also showed associations with fertilization rate; fertilization rate of oocytes obtained from TT cows was 63% vs. 68% for GT and GG cows. FGF2 SNP11646 did not show significant association with fertilization rate. However, interestingly, two way interaction between SNP23 and SNP11646 showed significant effects on fertilization rate (P=4.90E-03). The genotype combination of TT(SNP23) and AA(SNP11646) was associated with the lowest fertilization rate (62%) compared to all other genotype combinations.

TABLE 2

Association tests (P values) between individual genes and embryo survival rate, genotypes of ovaries, number of embryos, and observed survival rates

| Gene | P value | Genotype | Ovaries | Embryos | Survival rate |
|---|---|---|---|---|---|
| GHR | 3.80E-06 | AA | 256 | 3131 | 0.37 |
| | | AT | 125 | 1426 | 0.29 |
| | | AT | 17 | 153 | 0.28 |
| STAT5A | 1.37E-07 | GG | 87 | 902 | 0.31 |
| | | GC | 232 | 2762 | 0.33 |
| | | CC | 85 | 1113 | 0.40 |
| UTMP | 0.00039 | GG | 140 | 1735 | 0.30 |
| | | GA | 167 | 1924 | 0.36 |
| | | AA | 112 | 1266 | 0.36 |
| STAT1 | 0.115 | CC | 189 | 2235 | 0.34 |
| | | CT | 180 | 2216 | 0.34 |
| | | TT | 33 | 356 | 0.38 |
| FGF2 SNP 11646 | 3.69E-04 | GG | 130 | 1424 | 0.38 |
| | | AG | 207 | 2343 | 0.32 |
| | | AA | 107 | 1281 | 0.32 |
| FGF2 SNP23 | 6.87E-04 | GG | 263 | 3080 | 0.36 |
| | | GT | 121 | 1370 | 0.30 |
| | | TT | 22 | 221 | 0.29 |

TABLE 3

Association tests (P values) between individual genes and fertilization rate, genotypes of ovaries, number of fertilizations, and observed fertilization rate

| Gene | P value | Genotype | Ovaries | Fertilizations | Fertilization Rate |
|---|---|---|---|---|---|
| POU1 F1 | 0.0516 | CC | 279 | 4821 | 0.714 |
| | | AC | 51 | 918 | 0.677 |
| | | AA | 1 | 19 | 0.74 |
| GHR | 0.0647 | AA | 256 | 4473 | 0.70 |
| | | AT | 125 | 2154 | 0.66 |
| | | TT | 17 | 223 | 0.69 |
| STAT5A | 0.00371 | GG | 87 | 1360 | 0.66 |
| | | GC | 232 | 4028 | 0.69 |
| | | CC | 85 | 1574 | 0.71 |
| OPN | 0.00529 | TT | 142 | 2481 | 0.70 |
| | | TC | 204 | 3601 | 0.70 |
| | | CC | 48 | 739 | 0.62 |

TABLE 3-continued

Association tests (P values) between individual genes and fertilization rate, genotypes of ovaries, number of fertilizations, and observed fertilization rate

| Gene | P value | Geno-type | Ovaries | Fertil-izations | Fertil-ization Rate |
|---|---|---|---|---|---|
| STAT1 | 0.0298 | CC | 189 | 3176 | 0.70 |
| | | CT | 180 | 3261 | 0.68 |
| | | TT | 33 | 525 | 0.67 |
| FGF2 | 0.172 | GG | 263 | 4547 | 0.68 |
| SNP23 | | GT | 121 | 2015 | 0.68 |
| | | TT | 22 | 352 | 0.63 |

In the context of the present invention, the provided sequences also encompass the complementary sequence corresponding to any of the provided polymorphisms. In order to provide an unambiguous identification of the specific site of a polymorphism, the numbering of the original nucleic sequences in the GenBank is shown in the figures and is used.

The present invention provides nucleic acid based genetic markers for identifying bovine animals with superior fertility and survival traits. In general, for use as markers, nucleic acid fragments, preferably DNA fragments, will be of at least 12 nucleotides (nt), preferably at least 15 nt, usually at least 20 nt, often at least 50 nt. Such small DNA fragments are useful as primers for the polymerase chain reaction (PCR), and probes for hybridization screening, etc.

The term primer refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term primer site, or priming site, refers to the area of the target DNA to which a primer hybridizes. The term primer pair means a set of primers including a 5' upstream primer that hybridizes with the 5' end of the DNA sequence to be amplified and a 3', downstream primer that hybridizes with the complement of the 3' end of the sequence to be amplified.

The term “probe” or “hybridization probe” denotes a defined nucleic acid segment (or nucleotide analog segment) which can be used to identify by hybridization a specific polynucleotide sequence present in samples, said nucleic acid segment comprising a nucleotide sequence complementary of the specific polynucleotide sequence to be identified. “Probes” or “hybridization probes” are nucleic acids capable of binding in a base-specific manner to a complementary strand of nucleic acid.

An objective of the present invention is to determine which embodiment of the polymorphisms a specific sample of DNA has. For example, it is desirable to determine whether the nucleotide at a particular position is A or C. An oligonucleotide probe can be used for such purpose. Preferably, the oligonucleotide probe will have a detectable label, and contains an A at the corresponding position. Experimental conditions can be chosen such that if the sample DNA contains an A, they hybridization signal can be detected because the probe hybridizes to the corresponding complementary DNA strand in the sample, while if the sample DNA contains a G, no hybridization signal is detected.

Similarly, PCR primers and conditions can be devised, whereby the oligonucleotide is used as one of the PCR primers, for analyzing nucleic acids for the presence of a specific sequence. These may be direct amplification of the genomic DNA, or RT-PCR amplification of the mRNA transcript of the POU1F1 gene. The use of the polymerase chain reaction is described in Saiki et al. (1985) Science 230:1350-1354. Amplification may be used to determine whether a polymorphism is present, by using a primer that is specific for the polymorphism. Alternatively, various methods are known in the art that utilize oligonucleotide ligation as a means of detecting polymorphisms, for examples see Riley et al (1990) Nucleic Acids Res. 18:2887-2890; and Delahunty et al (1996) Am. J. Hum. Genet. 58:1239-1246. The detection method may also be based on direct DNA sequencing, or hybridization, or a combination thereof. Where large amounts of DNA are available, genomic DNA is used directly. Alternatively, the region of interest is cloned into a suitable vector and grown in sufficient quantity for analysis. The nucleic acid may be amplified by PCR, to provide sufficient amounts for analysis.

Hybridization may be performed in solution, or such hybridization may be performed when either the oligonucleotide probe or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid. For screening purposes, hybridization probes of the polymorphic sequences may be used where both forms are present, either in separate reactions, spatially separated on a solid phase matrix, or labeled such that they can be distinguished from each other.

Hybridization may also be performed with nucleic acid arrays and subarrays such as described in WO 95/11995. The arrays would contain a battery of allele-specific oligonucleotides representing each of the polymorphic sites, wherein the spatial location of each oligonucleic acid molecule is known. One or both polymorphic forms may be present in the array, for example the polymorphism of position 1296 may be represented by either, or both, of the listed nucleotides. Usually such an array will include at least 2 different polymorphic sequences, i.e. polymorphisms located at unique positions within the locus, and may include all of the provided polymorphisms. Arrays of interest may further comprise sequences, including polymorphisms, of other genetic sequences, particularly other sequences of interest. The oligonucleotide sequence on the array will usually be at least about 12 nt in length, may be the length of the provided polymorphic sequences, or may extend into the flanking regions to generate fragments of 100 to 200 nt in length. For examples of arrays, see Ramsay (1998) Nat. Biotech. 16:4044; Hacia et al. (1996) Nature Genetics 14:441-447; Lockhart et al. (1996) Nature Biotechnol. 14:1675-1680; and De Risi et al. (1996) Nature Genetics 14:457-460.

The identity of polymorphisms may also be determined using a mismatch detection technique, including but not limited to the RNase protection method using riboprobes (Winter et al., Proc. Natl. Acad. Sci. USA 82:7575, 1985; Meyers et al., Science 230:1242, 1985) and proteins which recognize nucleotide mismatches, such as the *E. coli* mutS protein (Modrich, P. Ann Rev. Genet. 25:229-253, 1991). Alternatively, variant alleles can be identified by single strand conformation polymorphism (SSCP) analysis (Orita et al., Genomics 5:874-879, 1989; Humphries et al., in Molecular Diagnosis of Genetic Diseases, R. Elles, ed., pp. 321-340, 1996) or denaturing gradient gel electrophoresis (DGGE) (Wartell et al., Nucl. Acids Res. 18:2699-2706, 1990; Sheffield et al., Proc. Natl. Acad. Sci. USA 86:232-236, 1989).

A polymerase-mediated primer extension method may also be used to identify the polymorphism(s). Several such methods have been described in the patent and scientific literature and include the "Genetic Bit Analysis" method (WO92/15712) and the ligase/polymerase mediated genetic bit analysis (U.S. Pat. No. 5,679,524). Related methods are disclosed in WO91/02087, WO90/09455, WO95/17676, U.S. Pat. Nos. 5,302,509, and 5,945,283. Extended primers containing a polymorphism may be detected by mass spectrometry as described in U.S. Pat. No. 5,605,798. Another primer extension method is allele-specific PCR (Ruao et al., Nucl. Acids Res. 17:8392, 1989; Ruao et al., Nucl. Acids Res. 19, 6877-6882, 1991; WO 93/22456; Turki et al., J. Clin. Invest. 95:1635-1641, 1995). In addition, multiple polymorphic sites may be investigated by simultaneously amplifying multiple regions of the nucleic acid using sets of allele-specific primers as described in Wallace et al. (WO 89/10414).

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethy-6-carboxyrhodamine (TAMRA), radioactive labels, e.g. .sup.32P, .sup.35S, .sup.3H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

It is readily recognized by those ordinarily skilled in the art that in order to maximize the signal to noise ratio, in probe hybridization detection procedure, the polymorphic site should at the center of the probe fragment used, whereby a mismatch has a maximum effect on destabilizing the hybrid molecule; and in a PCR detection procedure, the polymorphic site should be placed at the very 3'-end of the primer, whereby a mismatch has the maximum effect on preventing a chain elongation reaction by the DNA polymerase. The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center," and so on.

In some embodiments, a composition contains two or more differently labeled oligonucleotides for simultaneously probing the identity of nucleotides or nucleotide pairs at two or more polymorphic sites. It is also contemplated that primer compositions may contain two or more sets of allele-specific primer pairs to allow simultaneous targeting and amplification of two or more regions containing a polymorphic site.

Alternatively, the relevant portion of the gene of the sample of interest may be amplified via PCR and directly sequenced, and the sequence be compared to the wild type sequence shown in the figures. It is readily recognized that, other than those disclosed specifically herein, numerous primers can be devised to achieve the objectives. PCR and sequencing techniques are well known in the art and reagents and equipments are readily available commercially.

DNA markers have several advantages; segregation is easy to measure and is unambiguous, and DNA markers are co-dominant, i.e., heterozygous and homozygous animals can be distinctively identified. Once a marker system is established selection decisions could be made very easily, since DNA markers can be assayed any time after a blood sample can be collected from the individual infant animal, or even earlier by testing embryos in vitro if very early embryos are collected. The use of marker assisted genetic selection will greatly facilitate and speed up cattle breeding problems. For example, a modification of the multiple ovulation and embryo transfer (MOET) procedure can be used with genetic marker technology. Specifically, females are superovulated, eggs are collected, in vitro fertilized using semen from superior males and implanted into other females allowing for use of the superior genetics of the female (as well as the male) without having to wait for her to give birth to one calf at a time. Developing blastomeres at the 4-8 cell stage may be assayed for presence of the marker, and selection decisions made accordingly.

In one embodiment of the invention an assay is provided for detection of presence of a desirable genotype using the markers.

The term "genotype" as used herein refers to the identity of the alleles present in an individual or a sample. In the context of the present invention a genotype preferably refers to the description of the polymorphic alleles present in an individual or a sample. The term "genotyping" a sample or an individual for a polymorphic marker refers to determining the specific allele or the specific nucleotide carried by an individual at a polymorphic marker.

The present invention is suitable for identifying a bovine, including a young or adult bovine animal, an embryo, a semen sample, an egg, a fertilized egg, or a zygote, or other cell or tissue sample therefrom, to determine whether said bovine possesses the desired genotypes of the present invention, some of which are indicative of improved milk production traits.

Further provided is a method for genotyping one of the bovine genes listed in Table 1, comprising determining for the two copies of the gene present the identity of the nucleotide pair at the relevant SNP position.

One embodiment of a genotyping method of the invention involves examining both copies of the gene, or a fragment thereof, to identify the nucleotide pair at the polymorphic site in the two copies to assign a genotype to the individual. In some embodiments, "examining a gene" may include examining one or more of: DNA containing the gene, mRNA transcripts thereof, or cDNA copies thereof. As will be readily understood by the skilled artisan, the two "copies" of a gene, mRNA or cDNA, or fragment thereof in an individual may be the same allele or may be different alleles. In another embodiment, a genotyping method of the invention comprises determining the identity of the nucleotide pair at the polymorphic site.

The present invention further provides a kit for genotyping a bovine sample, the kit comprising in a container a nucleic acid molecule, as described above, designed for detecting the polymorphism, and optionally at least another component for carrying out such detection. Preferably, a kit comprises at least two oligonucleotides packaged in the same or separate containers. The kit may also contain other components such as hybridization buffer (where the oligonucleotides are to be used as a probe) packaged in a separate container. Alternatively, where the oligonucleotides are to be used to amplify a target region, the kit may contain, preferably packaged in separate containers, a polymerase and a reaction buffer optimized for primer extension mediated by the polymerase, such as PCR.

In one embodiment the present invention provides a breeding method whereby genotyping as described above is conducted on bovine embryos, and based on the results, certain cattle are either selected or dropped out of the breeding program.

Through use of the linked marker loci, procedures termed "marker assisted selection" (MAS) may be used for genetic improvement within a breeding nucleus; or "marker assisted introgression" for transferring useful alleles from a resource population to a breeding nucleus (Soller 1990; Soller 1994).

The present invention discloses the association between the genes listed in Table 1 and fertilization rate or embryonic survival.

The following examples are intended to illustrate preferred embodiments of the invention and should not be interpreted to limit the scope of the invention as defined in the claims.

The sequence listing txt file in computer readable form, named "Sequence Listing", having a size of 28.18 KB and created on Jun. 12, 2018, is incorporated by reference herein.

REFERENCES CITED

Akers, R. M. 2006. Major advances associated with hormone and growth factor regulation of mammary growth and lactation in dairy cows. J. Dairy Sci. 89(4):1222-1234.

Bagnato, A., F. Schiavini, A. Rossoni, C. Maltecca, M. Dolezal, I. Medugorac, J. Solkner, V. Russo, L. Fontanesi, A. Friedmann, M. Soller, and E. Lipkin. 2008. Quantitative trait loci affecting milk yield and protein percentage in a three-country Brown Swiss population. J. Dairy Sci. 91:767-783.

Bastos, E., I. Santos, I. Parmentier, J. L. Castrillo, A. Cravador, H. Guedes-Pinto, and R. Renaville. 2006. Ovis cries POU 1F1 gene: cloning, characterization and polymorphism analysis. Genetic a 126(3): 303-314.

Cobanoglu, 0., I. Zaitoun, Y. M. Chang, G. E. Shook, and H. Khatib. 2006. Effects of the signal transducer and activator of transcription 1 (STAT1) gene on milk production traits in Holstein dairy cattle. J. Dairy Sci. 89(11):4433-4437.

Falconer, D. S. and T. F. C. Mackay. 1996. Introduction to Quantitative Genetics. 4th ed. Addison Wesley Longman Limited, England.

Georges, M., D. Nielsen, M. Mackinnon, A. Mishra, R. Okimoto, A. T. Pasquino, L. S. Sargeant, A. Sorensen, M. R. Steele, X. Zhao, and et al. 1995. Mapping quantitative trait loci controlling milk production in dairy cattle by exploiting progeny testing. Genetics 139(2):907-920.

Gonda, M. G., Y. M. Chang, G. E. Shook, M. T. Collins, and B. W. Kirkpatrick. 2006. Genetic variation of *Mycobacterium avium* ssp. paratuberculosis infection in US Holsteins. J. Dairy Sci 89(5):1804-1812.

OcOn-Grove, 0. M., F. N. Cooke, I. M. Alvarez, S. E. Johnson, T. L. Ott, and A. D. Ealy A D. 2007. Ovine endometrial expression of fibroblast growth factor (FGF) 2 and conceptus expression of FGF receptors during early pregnancy. Domest. Anim. Endocrinol. (In press).

Ingraham, H. A., R. P. Chen, H. J. Mangalam, H. P. Elsholtz, S. E. Flynn, C. R. Lin, D. M. Simmons, L. Swanson, and M. G. Rosenfeld. 1988. A tissue-specific transcription factor containing a homeodomain specifies a pituitary phenotype. Cell 55(3):519-529.

Ingraham, H. A., S. E. Flynn, J. W. Voss, V. R. Albert, M. S. Kapiloff, L. Wilson, and M. G. Rosenfeld. 1990. The POU-specific domain of Pit-1 is essential for sequence-specific, high affinity DNA binding and DNA-dependent Pit-1-Pit-1 interactions. Cell 61(6):1021-1033.

Khatib, H., E. Heifetz, and J. C. Dekkers. 2005. Association of the protease inhibitor gene with production traits in Holstein dairy cattle. J. Dairy Sci 88(3):1208-1213.

Khatib, H., S. D. Leonard, V. Schutzkus, W. Luo, and Y. M. Chang. 2006. Association of the OLR1 gene with milk composition in Holstein dairy cattle. J. Dairy Sci. 89(5): 1753-1760.

Khatib, H., G. J. Rosa, K. Weigel, F. Schiavini, E. Santus, and A. Bagnato. 2007a. Additional support for an association between OLR1 and milk fat traits in cattle. Anim. Genet.

Khatib, H., V. Schutzkus, V. M. Chang, and G. J. Rosa. 2007b. Pattern of expression of the uterine milk protein gene and its association with productive life in dairy cattle. J. Dairy Sci. 90(5):2427-2433.

Khatib, H., R. L. Monson, V. Schutzkus, D. M. Kohl, G. J. M. Rosa, and J. J. Rutledge. 2008a. Mutations in the STAT5A Gene are Associated with Embryonic Survival and Milk Composition in Cattle. J. Dairy Sci. 91:784-793.

Khatib, H., C. Maltecca, R. L. Monson, V. Schutzkus, X. Wang, and J. J. Rutledge. 2008b. The fibroblast growth factor 2 gene is associated with embryonic mortality in cattle. J. Anim Sci. 86:2063-2067.

Leonard, S., H. Khatib, V. Schutzkus, V. M. Chang, and C. Maltecca. 2005. Effects of the osteopontin gene variants on milk production traits in dairy cattle. J. Dairy Sci. 88(11):4083-4086.

Li, S., E. B. Crenshaw, 3rd, E. J. Rawson, D. M. Simmons, L. W. Swanson, and M. G. Rosenfeld. 1990. Dwarf locus mutants lacking three pituitary cell types result from mutations in the POU-domain gene pit-1. Nature 347 (6293):528-533.

Lipkin, E., R. Tal-Stein, A. Friedmann, and M. Soller. 2008. Effect of quantitative trait loci for milk protein percentage on milk protein yield and milk yield in Israeli Holstein dairy cattle. J. Dairy Sci. 91:1614-1627.

Liu, X., G. W. Robinson, K. U. Wagner, L. Garrett, A. Wynshaw-Boris, and L. Hennighausen. 1997. Stat5a is mandatory for adult mammary gland development and lactogenesis. Genes Dev. 11(2):179-186.

Lucy, M. C. 2001. Reproductive loss in high-producing dairy cattle: where will it end? J. Dairy Sci. 84:1277-1293.

Michael, D. D., I. M. Alvarex, 0. M. ° con, A. M. Powell, N. C. Talbot, S. E. Johnson, and A. D. Ealy. 2006. Fibroblast growth factor-2 is expressed by the bovine uterus and stimulates interferon-tau production in bovine trophectoderm. Endocrinology 147: 3571-3579.

Mullis, P. E. 2007. Genetics of growth hormone deficiency. Endocrinol. Metab. Clin. North Nadesalingam, J., Y. Plante, and J. P. Gibson. 2001. Detection of QTL for milk production on Chromosomes 1 and 6 of Holstein cattle. Mamm. Genome 12(1):27-31.

Renaville, R., N. Gengler, E. Vrech, A. Prandi, S. Massart, C. Corradini, C. Bertozzi, F. Mortiaux, A. Burny, and D. Portetelle. 1997. Pit-1 gene polymorphism, milk yield, and conformation traits for Italian Holstein-Friesian bulls. J. Dairy Sci. 80(12):3431-3438.

Royal, M., G. E. Mann, and A. P. Flint. 2000. Strategies for reversing the trend towards subfertility in dairy cattle. Vet. J. 160:53-60.

Schnabel, R. D., J. J. Kim, M. S. Ashwell, T. S. Sonstegard, C. P. Van Tassell, E. E. Connor, and J. F. Taylor. 2005. Fine-mapping milk production quantitative trait loci on BTA6: analysis of the bovine osteopontin gene. Proc. Natl. Acad. Sci. L S A 102(19):6896-6901.

Svennersten-Sjaunja, K. and K. Olsson. 2005. Endocrinology of milk production. Domest Anim Endocrinol 29(2): 241-258.

Tuggle, C. K. and A. E. Freeman, Inventors. 1994. Genetic marker for improved milk production traits in cattle. Iowa State University Research Foundation, Inc., assignee. U.S. Pat. No. 5,614,364.

Veerkamp, R. F., and B. Beerda. 2007. Genetics and genomics to improve fertility in high producing dairy cows. Theriogenology 68S:S266-S273.

Viitala, S., J. Szyda, S. Blott, N. Schulman, M. Lidauer, A. Maki-Tanila, M. Georges, and J. Vilkki. 2006. The role of the bovine growth hormone receptor and prolactin receptor genes in milk, fat and protein production in Finnish Ayrshire dairy cattle. Genetics 173(4):2151-2164.

Wang, X., C. Maltecca, R. Tal-Stein, E. Lipkin, and H. Khatib. 2008. Association of bovine fibroblast growth factor 2 (FGF2) gene with milk fat and productive life: an example of the ability of the candidate pathway strategy to identify quantitative trait genes. J. Dairy Sci. 91:2475-2480.

Weller, J. I., Y. Kashi, and M. Soller. 1990. Power of daughter and granddaughter designs for determining linkage between marker loci and quantitative trait loci in dairy cattle. J. Dairy Sci 73(9):2525-2537.

Woollard, J., C. K. Tuggle, and F. A. Ponce de Leon. 2000. Rapid communication: localization of POU1F1 to bovine, ovine, and caprine 1q21-22. J Anim Sci 78(1):242-243.

What is claimed is:

1. A method for selectively breeding dairy cattle, comprising selecting a bull cattle that comprises a bovine fibroblast growth factor 2 (FGF2) gene which comprises guanine at position 23 of SEQ ID NO: 6 or guanine at position 11646 of SEQ ID NO: 6 wherein guanine at one of the recited positions is correlated with increases of at least one of a fertilization rate or an embryo survival rate relative to cattle without a guanine at the recited positions; and using its semen to fertilize a female cattle.

2. A method according to claim 1, wherein a bull cattle is selected, the bovine FGF2 gene of which is homozygous for guanine at position of 23 of SEQ ID NO: 6 or guanine at position 11646 of SEQ ID NO: 6.

3. The method according to claim 1, wherein the female cattle also comprises a bovine FGF2 gene which comprises guanine at position of 23 of SEQ ID NO: 6 or guanine at position 11646 of SEQ ID NO: 6.

4. The method according to claim 1, wherein the female cattle also comprises a bovine FGF2 gene homozygous for guanine at position of 23 of SEQ ID NO: 6 or guanine at position 11646 of SEQ ID NO: 6.

5. The method according to claim 1, wherein the female cattle is in vitro fertilized.

6. The method of claim 1, wherein a multiple ovulation and embryo transfer (MOET) procedure is used.

* * * * *

SEQUENCE LISTING

<160> NUMBER OF SEQ ID NOS: 9

<210> SEQ ID NO 1
<211> LENGTH: 1463
<212> TYPE: DNA
<213> ORGANISM: Bos taurus
<220> FEATURE:
<221> NAME/KEY: misc_feature
<222> LOCATION: (1296)..(1296)
<223> OTHER INFORMATION: r is a or g

<400> SEQUENCE: 1
ggctggattg ccgcagaaat gtcccacggg agaatgaatc tggccctgtc tctggtcttc 60
atcctctgtg gcctgtttaa tagcatcttc tgtgaaaagc aacaacactc tcaaaagcac 120
atgaacctag tcttattaaa gaaaatttca gctctctccc agaagatgga agctcaccct 180
aaggattttg cccaagaatt gttcaaggct ttgataattg aggatcccag aaagaatatc 240
atcttctccc ccatggccat gaccaccacc ctggccaccc tctccctggg gatcaagtct 300
acaatgagaa cccaccaccc tgaggacctg aaacttgagc ccaaactgtt ggatgtgcac 360
aagtacttac agcctctggt ccacgtgggg cgtgagctag tgaagcagaa ggtactgaag 420
caccagcaca ttctctttat caacagaaaa atgatggtca accagatgct tctacagcag 480
ataagcaagc tgcagggaat ggacatccag atgattgact ttacagatat agaaaaagcc 540
aagaagacca tcagccacca tgtggctgaa aaaacacata cgaaaatcac aaacttaatc 600
accgacctga accctgagac catcctgtgt cttgttaacc acattttctt caaaggcatc 660

-continued ttgaaaagag cttttcagcc caaactcacc cagaaggagg tcttctttgt gaatgaccaa 720
accaaagtgc aggtggacat gatgagaaag acagaacgga tgctttacag ccggtcagag 780
gagctacatg ctacgatggt taagatgcct tgcaaaggaa atgtgtccct aactctcatg 840
cttccagatg ccggacaatt tgacactgat cttaaaaaga tgactgctaa gcgagctaaa 900
cttcagaaaa tcagtgactt cagactggtg cgcttaattt tgcccaagtt gaagatctcc 960
ttcaagataa actttaagca tctgcttccc aagattgacc ccaaacatat actgactgcc 1020
acagcaatct cacaggccat cacatcgaag gctcccctgc ctaatttgga ggccctacat 1080
caagctgaga tagagctgag cgagcacgcc ttaaccgtgg acacagccat tcacacagat 1140
aatctgttga aagtcccagt gaaggcaaag gaggtcccgg cggtcgtgaa agtcccaatg 1200
aaggcaaagg aggtcccggc ggtcgtgaaa gtcccaatga acacaaagga ggtcccagtg 1260
gtcgtgaaag tcccaatgaa cacaaaggag gtcccrgtgg tcgtgaaggt caacagaccc 1320
ttcttgctgt ttgtggagga tgagaagact caaagagacc tctttgtggg caaagtcctc 1380
aacccccaag ttgagtagag ccagggccac actgtgcagc acaggaactt agcaggccat 1440
gaataaaaag agtacaattc acc 1463

<210> SEQ ID NO 2
<211> LENGTH: 626
<212> TYPE: DNA
<213> ORGANISM: Bos taurus
<220> FEATURE:
<221> NAME/KEY: misc_feature
<222> LOCATION: (213)..(213)
<223> OTHER INFORMATION: y is c or t

<400> SEQUENCE: 2
ctttaaatat agcctcaagt ttgccagtgg cttgcctgtg aaatagtgca aagctgtcct 60
gtatctgggc agaggataaa agttatgtgt gttattatat tttccacact ggccattgaa 120
aactaaagat tctctttctt gggagaatta gcttttggta tggctttatg atgctggcta 180
atatcaatag aaggaagtaa actttacaaa ttyatgagta gtatcttcca tttcagcttt 240
aataccaaag ttgaatatat tctgccttca tcatgaaatt gaagttagta aatgaaactg 300
tcttcacagt tctatcaagg gagccaaact attaacagct ctcttaaggc aaatcctatt 360
attttttcaa aaagttgaaa ttaattgtag atgtaaacaa actcagaaat ttaatgcatg 420
tttcataagt gggttcactt gtctttattg tttagtaaaa attttaaaat tgagaagaaa 480
aactagtaat tgacaaatca ttaggtggag attatgagaa tccaataatt tgaaaactca 540
tcctgtgtaa ctgccttgag aattgggtaa ttttcactgg caaatgtgta tctctcacaa 600
atacattaca gatggttcca ctaaaa 626

<210> SEQ ID NO 3
<211> LENGTH: 1560
<212> TYPE: DNA
<213> ORGANISM: Bos taurus
<220> FEATURE:
<221> NAME/KEY: misc_feature
<222> LOCATION: (944)..(944)
<223> OTHER INFORMATION: y is t or c

<400> SEQUENCE: 3
taattaactc taaatattaa aattctcaca attaaagaac aaccactcca aaaaatagcc 60
accaagcagg ccatttgggc tggttaaatg gatcttccct gcctgttggg cttccctgat 120
agctcagttg gtaaagcatc tgcctgcaac ttggaagacc cgggttcagt ccctgggtcg 180

```
ggaagactcc ctggagaagg aaatggcaac cccctctagt actcttgcct ggaaaatttc    240

catggactga ggaccctggt aggctaagag tcagacagaa ctgagcaact tcacttcact    300

ttcctgcctg tttgtaaaag tgagcttagg acaccaattg atctgtcagg ttgtcttccg    360

gcttaatcct tccacaatga ggctagaaaa ataagacctg ctttggatgg aaacagctaa    420

cttttgaata aaaaagttac gttgtatgat gtgcactgat ttgtgtcttt tcttcttcag    480

aattctgtgt cctctgagga aactgatgac aacaaacaaa atgtgagtct ttgctttgat    540

tctgatgtct gttgtgcctt agactcagga aggcactctt tctcctaatg acattgccca    600

ggttcaaatt ccggcaaaat tccactagca aacccttcag gaactacttt ttattgggac    660

tattaatagg gataagttaa atttgctttc cttaagattc tatttgaaga tgctgagaat    720

ctataagaga agttagataa atgacccagg atatttgcaa atcagaagtg tgatagacat    780

taactgagct atagtttcta cacatggata agagagtcac cttttgatta tccaggctaa    840

tagggaggtg attttagttt tgggggtgtg cattaataca tggattctct gatcccctga    900

gaattttcat ttcaaataga aaaggtagtc tcacaattat gtayctgtat ttattggatc    960

attgaaattt ggtaaattag tgtttattat gaacaaggaa aaacagtgtc attgatacaa   1020

atattataac tcatacgttt ggcttgaaaa tatctgtgaa aatcgttttt atgagaaacc   1080

aagaaaaatg ccttagaata ggattccatt taccettgtg ttaaagggga aattggaata   1140

agctcatttt agcatttaaa agccattaag tgctttgttg tgaatacaaa gattctaaaa   1200

ctaaataaag atagtaaaat actaatgcac tgtaaagcct aagggacagt aaaaaccctg   1260

acacccattt ttctggccat cttgatttct agaccctccc aagtaagtcc aatgaaagcc   1320

ctgagcaaac agacgatcta gatgacgatg atgataacag ccaggacgtc aactctaatg   1380

actccgacga cgctgaaacc actgatgacc ctgaccattc cgacgagtct caccattctg   1440

atgaatctga tgaagttgat tttcccactg atattccaac aatcgcagtt ttcactccgt   1500

ttatccctac ggaaagcgca aatgatggcc gaggtgatag tgtggcttac ggactgaagt   1560
```

<210> SEQ ID NO 4
<211> LENGTH: 1380
<212> TYPE: DNA
<213> ORGANISM: Bos taurus
<220> FEATURE:
<221> NAME/KEY: misc_feature
<222> LOCATION: (703)..(703)
<223> OTHER INFORMATION: w is t or a

<400> SEQUENCE: 4

```
cagataatga aggataagga aggctggcat gctgcagttc atggggttgc aaagagtcag     60

acatgactta gcaactgaac agcattctaa aatctgagag tcctagtact gatcttctgt    120

caaacagtac tttttacgct gtaaaaatgt acaccctgca tatctaagaa gttttaataa    180

tgattcaaaa atacaacttg gcccccatct ttttgatgga tcctcagtct agatcagatc    240

tagatctaaa gatcacatta aaaaaaaaaa agaattggac attatttagg taaagtagta    300

tattaacaag catcactttt ccctcaagct aaagcctttt aatgacacac cctgaacaca    360

taagatgttt aaagcaggtt gtttatataa taaacatgga ttgtgcttaa attgtatgct    420

gttactcttt tttttttggt atacaaaagg atctgaagaa gtggatagag gtgttcttag    480

aaaatactaa gtaattgcat tctatttcag tggctatcaa gtgaaatcat tgactttact    540

agatgaatac aaattaggaa gttttatgtg gaacaggaga atgagatata aacttcaact    600
```

-continued gttcatagtt ctgtgagata ttatttttgt gtttttcaga tttccagttt ccatggttct 660
taattattat ctttggaata cttgggctag cagtgacatt atwtttactc atattttcta 720
aacagcaaag gtaagtgtga tataacctac tctgatatgt tttgccagtt atttagcaaa 780
tgtccatgtt tccatttttt gtttgatgtt ttcttttgtg aatcctgagt gaagtgtttc 840
atcaacccag tgaaacgtta tcgctctaca tttacatctt tgttgtgtcc acagagagac 900
aacacaggtc tcagttttat ctggaaagtt gcataggatg ttaagagggt gaggctagtg 960
actacatacc atgtgacatg caccttaaag ttccgcactg atatttattc caggacccag 1020
aggtagcttt gagcaaaaat ttaagtggtg aactaaagct actagataat tcagtctaat 1080
aaaacctttc tttagacttc atatgatacc aatcttaagt aaatttgggt ttatttaaat 1140
tggttggcta cttacagttt ggtattttac cttcttttgt cagagataaa attctaagtt 1200
tgaggacacc atcctgcatc ctcttgcagc cagaaggcag gtttcagtta ttattctgcc 1260
actgttgttt gagttcattt gagtcccttt atctctagga ctccacgttc tcatgggtaa 1320
tttgagggtg gtggattgta tgatgtttaa gtttccctta agctgtaagg accattattc 1380

<210> SEQ ID NO 5
<211> LENGTH: 1505
<212> TYPE: DNA
<213> ORGANISM: Bos taurus
<220> FEATURE:
<221> NAME/KEY: misc_feature
<222> LOCATION: (577)..(577)
<223> OTHER INFORMATION: m is c or a
<220> FEATURE:
<221> NAME/KEY: misc_feature
<222> LOCATION: (1308)..(1310)
<223> OTHER INFORMATION: n is a, c, g, or t
<220> FEATURE:
<221> NAME/KEY: misc_feature
<222> LOCATION: (1334)..(1334)
<223> OTHER INFORMATION: n is a, c, g, or t
<220> FEATURE:
<221> NAME/KEY: misc_feature
<222> LOCATION: (1391)..(1391)
<223> OTHER INFORMATION: n is a, c, g, or t
<220> FEATURE:
<221> NAME/KEY: misc_feature
<222> LOCATION: (1406)..(1410)
<223> OTHER INFORMATION: n is a, c, g, or t
<220> FEATURE:
<221> NAME/KEY: misc_feature
<222> LOCATION: (1414)..(1414)
<223> OTHER INFORMATION: n is a, c, g, or t
<220> FEATURE:
<221> NAME/KEY: misc_feature
<222> LOCATION: (1421)..(1421)
<223> OTHER INFORMATION: n is a, c, g, or t
<220> FEATURE:
<221> NAME/KEY: misc_feature
<222> LOCATION: (1495)..(1495)
<223> OTHER INFORMATION: n is a, c, g, or t

<400> SEQUENCE: 5
gcaaatactg tgatttgaag ctaaccaaat aaactaattt ctattttggc tggagaagag 60
aaaggaatga aagtagaaac actcgctatt acacatagga gagcctatct gaattcgaga 120
tgctccttag aaatagtaaa taaactctga ttcaggcttg tcttcacccg tttttctctc 180
tgcttcggtt acaaaaccaa accctcacca cttctttctc caggtttagt tcttcagcca 240
tccgcaggat ctcctgagag gaaggcttat tctgttctcc aaagtgtctc tccagggcgt 300
ctttagcagc aatactgatt gttgttctcc gtttctattc ttttgtggga atgagttgcc 360 aacctttac ttcgactgat acctttatac ctctgaattc tgagtcttct gcaactctgc 420

```
ctctgataat gcatcccagt gctgcggagt gcctaccggt ctccaaccac gccaccaacg    480

tgatgtccac agcaacagga cttcattatt ctgttccttt ctgtcattat ggaaaccagt    540

catcgaccta tggcgtgatg gcagggagct taacccmttg tctttataag tttcctgacc    600

acacgttgag tcatggtttt cctcccatgc atcagcctct cctttcagag gaccccactg    660

ccgctgattt caagcaggag ctcaggcgga aaagcaaatt ggttgaagag ccaatagaca    720

tggattctcc agaaatccga gaacttgaaa agtttgccaa tgagtttaaa gtgagaagaa    780

ttaagctagg atacacccag acaaatgttg ggaagctctt ggcagctgtg catggctctg    840

aattcagtca aacaactatc tgccgatttg aaaacctgca gctcagcttc aaaaatgcat    900

gcaaactaaa agcaatatta tccaaatggc tggaggaagc cgagcaagta ggagctttat    960

acaatgagaa agttggtgca aatgaaagaa aaaggaaacg gagaacaaca atcagtattg   1020

ctgctaaaga cgcgctggag agacactttg gagaacagaa taagccttcc tctcaggaga   1080

tcctgcggat ggctgaagaa ctaaacctgg agaaagaagt ggtgagggtt tggttttgta   1140

accgaaggca gagagaaaaa cgggtgaaga caagcctaaa tcagagttta tttactattt   1200

ctaaggagca tctcgaatgc agataggctc tcctattgtg taatagcgat tctacttttc   1260

attcctttct cttctcagcc aaaatagaaa ttagttattt ggttagcnnn aaaaatcaca   1320

tcagtaattt ttgncagaag tgtttctttt ctactttaaa aataaataca atttaaatta   1380

tgttgatgaa ntattctcag aaggannnnn tcantgtaca ntttaagcca aagactaata   1440

ggattaaaac aatgattctg tccctttcac tatatctttc cctctatctc tcccnggaat   1500

tcttc                                                               1505
```

<210> SEQ ID NO 6
<211> LENGTH: 12110
<212> TYPE: DNA
<213> ORGANISM: Bos taurus
<220> FEATURE:
<221> NAME/KEY: misc_feature
<222> LOCATION: (23)..(23)
<223> OTHER INFORMATION: k is g or t
<220> FEATURE:
<221> NAME/KEY: misc_feature
<222> LOCATION: (11646)..(11646)
<223> OTHER INFORMATION: r is a or g

<400> SEQUENCE: 6

```
ccggggccgc gccgcggagc gcktcggagg ccggggccgg ggcgcggcgg ctccccgcgc     60

ggctccaggg gctcggggac cccgccaggg ccttggtggg gccatggccg ccgggagcat    120

caccacgctg ccagtccctg ccggaggacg gcggcagcgg cgctttcccg ccgggccact    180

tcaaggaccc caagcggctg tactgcaaga acgggggctt cttcctgcgc atccaccccg    240

acggccgagt ggacggggtc cgcgagaaga gcgacccaca cagtgagtgc tccccaggtc    300

ttccccggtg ccgtcttcgt cccctgcggt tctctccccc gcccctgcct tccagcctcc    360

gcgctccttc ttcctcttca ctgtgacccc ggtgggactt gtggtttctc tccgctcggc    420

cctcggcggt ttcgggctca ccactcgccc ccctcctgcc ccgagctgcg gtggcggtag    480

acgctcctcc aggctttgga gtgtgccggc tgctcagcaa agccagtccc ctgggccccg    540

agcccccggc gcccgggctt tgcgggcggc tccctgggcg cagacaacct gtcgcgtcgg    600

gggtgcccgg cggctgagca gaggtgagcg gctcagcgag gtgccgcccg cgccccgagc    660

ctgaagttcc gaccgcttct atgggatgcc cgttgtctcc ggggcaaagc caggagggac    720
```

-continued

```
cgcagaccaa ctaaaaggtc cttgttggaa agataccttg catcaggttt gaggatcaaa    780
tgagaatttg aagtgcgcag aggactcaat ttactagtct acagttgcat tttctgtaaa    840
aataataatg atgtatctgt ggtaatagca ataagattgg tctgaggcgt tggttgtcaa    900
actaagagtg cataagaatc acctggaagg tgtgtgtgtt gtgtgattca tggctgaacc    960
atctcccaga gtttcagatc gcttaggtct ggagtggggc ctcatttgca tttctaacta   1020
cttcccaggt gatgctgatc tgggagcaca gtttgagaac ccgctggtct agagaaagag   1080
gaaggaaaga ggtataaaat gggctgataa aaatagatga gtttgaagtg agacaaagag   1140
atcagatatt tttaaactgt catcctgtaa gtgtaggtaa aacatgtttt gaaagctgtt   1200
tgttctgcca ttccttccat aatggttttc aggtggaaaa cttgatcctc tttttttttt   1260
tttttttttg cccaagttcc gcaagaggcc ttctttacct tgtgatgcta atagtgcgtc   1320
ctttggggct ctccaggtgg tactggtggt aaagatccca cctgccagtg cctgggatgt   1380
aagaggtgtg gattggatcc ctgtgttgga aagatcccct ggagaaggaa atggcacccc   1440
gctccagtat tcttgcctgg agactcccca tggacagagg agcctagtgg gctaccgtcc   1500
ctagggtccc aaagagtcgg acactgaagg aatttagcaa gctctcactc cgggatgaga   1560
cttaggaaga ggagaaaact ctgcagccaa acctagctga caaattcagt aatgggaaat   1620
gtcccttcat aagaattggt ctttattgat ttcaaaatag caacaagcaa aggattcagg   1680
tctgtaactt ttttccggcc tgccataatt aaacaatttt cttaaccact tacattatcc   1740
agtaaaactg aaaagatgct tgtagcccaa tatatcggtt agtgctcttt ctctattttg   1800
gtaactaggt ttcacaaaat tatctttctg tgtggggttt attctgtgct tgtctgccag   1860
ggtagcccag ctgaacacgg caaggtgcac atatgtccca attaattttg ctcttttcta   1920
gtatcacaaa aagtagtttg ttctttgacg agaagacaga actcttcccc cagattaggt   1980
ttatactgga gcttccttta gtacattttc ttccagacat tttatgagtt gcagtatttt   2040
ctttgccttc tcaataccct atttccttta aaacaaaact gtataggggc tgggctttcc   2100
aggtggcgca gtggtaagga atccgcctgc caatatagga gatgcaggag acactcgttc   2160
aatccctgga ttgggtagat cccctggaaa agggaatggc aaccaactcc agtattcttg   2220
cctgggaaat cccatgagtg gaggagcctg gcaggcacag tccagggggt cccagaaaat   2280
cagacgtgac tgagcacaca ggcatgtatg ggagttagta aggataattc tgaattgcat   2340
attacattac cgccctttta aacacaacta ttaacttttt attcccagtt tggggctggg   2400
ccatcattac tgtattctta ttttaacttc atggtctgaa ataggattga tactctccag   2460
gggacatttg gcagtgcctg gagatgtttt cactcatgcc tggaagggtg ctactgtcat   2520
ttgctaagta gaggccaggg atgttacagt gcacaggaca cctccctaat cgctcagcaa   2580
aaaattaaaa atgttctgac cgtaaatgtt aatagtgtta aggctgagaa acccagccaa   2640
cctgataact agctcgtaga cctttaaagg tagagagtag agtactcatc cagacttgtg   2700
gagagcactg atttttaaaa atcaccttgt accaggtggt agactgacaa gaatagaaac   2760
ctgaaaatga tcaatttaaa tgacttttgt ataggccaac ctggacatat gtttaattaa   2820
ggacagtgtt tttttttttt tttcccctga catatcaaag gtgtactgat agttgacaaa   2880
accaggagga gacaggtaag aaatatatag gaaaaacaat gccatatcag tatcctctta   2940
accatatccc ctccattccc ctaaaggagc aaaactgatc ggcaaacgtg gagaaataaa   3000
agctgttaat gcttgctaca gcttcccacc gaattaaggt tcagagatct agacatattt   3060
gaaacattgg aaaatccaag gccccctccc tcaaactcat ttgtccatac acccaaaatc   3120
```

-continued

```
tatcactgga gatttatccc tttggcatta actctctgtc cagatgtttc taaaatgcaa   3180
atgcagtgtg ctctccgaat ccacagtctc catctgtggt gatgacagcc gacggcccta   3240
caccgttttc cacgagggac ttgagcctcg gcgggtgctg gaaaccctgg acccgggtcc   3300
tcatgggtac ggggtggagg gtgcctctgg aaggacaagt ggagcagtta cccggtttta   3360
acatttcgtg tgaattaaat tgtatgtgca tgatttcttc cccaaaagct gaccagcagg   3420
gctggagttg agggggagg ctgtgaagtc ggtggcatga atgtggggca ctggtcaggg   3480
gcaggggaca tggctaggtt ctgaagggac atagggcagg acggtgtggg gctgggcgga   3540
cagcgtttcc agcttcccac ttttgctgga gatcacctgt gtttctcccc gggttttctc   3600
ttgaattgtt ttcacaattg tttcaaaagg cccactttcc tgcacttttc tcacaatcct   3660
gaaataacct gtatttgaca cgagtgtgtt ggtaaaagcg agataaagac agggccagcg   3720
tgggtgccgc acatccacct tccctttggt gtcccacttg cccacgggga tgtgtaacag   3780
aagtatatgc cctgaagtac tgaaaccatg tgaaaacatt cggaagagag cacattttat   3840
cccaggcagc acgttcaaca tgtggtggag tatagtcagg gcaaagtatg ctgcttgtgt   3900
acattttagc attaaattta ttccagatgc ttttattttg gaaaaaacga aggtagttaa   3960
aagtgctaga tcgacctttg ggtcttctcc caggaggtga ccgcctgctt gccacactcc   4020
tctggcttcc ggcctccaga ggacactgag ccttgaagag gctgagggac ctgcccaccc   4080
ccaagtggag cagggctggg atcccgtctg actcccaccc tctgtgccac cgcacatatt   4140
ccatgcagcc ccgtcattaa aaacgaactg ttcaccagct tcatcttgta gaagacgaga   4200
ttgaggtcca caggcggaac tgattgccgg agtttacctg ccgattcttg cccacttgcc   4260
cccttgcgga ctgtccctgc tgttctggct ttttaggctt cctccacttc aaaatattga   4320
catagtcgct ctggggaggt cttatgagtc cacaggttgc ctctggttgt accccctgga   4380
gcaatgaaga aagccacctt ttcttctctt cctttatgtc aatggaactt ttgattgatg   4440
acaccagatt ctccccctc cacacacata cacctttttt gggtaatatc tggcaagtgg   4500
atcccaccaa tttactttaa taagcatact gtttactcta atgacatttg tgtgcagtaa   4560
acaaatgaag taagaaccca atagctcatt taattgtgga aatcgtgtaa ttggttcagc   4620
aatgaaagga caattcatga gtcatggata ttaccacacc ttaggagcct tttaaaatga   4680
gtttggtgcc aaatgacttc agcctagaac tggcaatatc ctcttgtgac atgccttgag   4740
ggctttcttt gtgtttataa agtggccatc ccataattgg attttgacag aggtatgaaa   4800
agtggattct gagcattatg ttcagactta cgatgtttta aatggatagc tgagattttt   4860
aggtgtaatt tgaaaaaacg ttatagacaa aacaagaatc atcctcaata cattataatt   4920
ataaaattga ctgttcatct acatattgat tctcagaaat tactctcagc gatattgaaa   4980
aaaggcagta taaggtctcg cattattaga attgttattt tctggccaaa agatgcctgt   5040
ggaacaggga ggtaactact catgtgccat tgcctttact tgtttttcaa aaccccctgc   5100
ttgggcccct ttgtcctaca acaaacatct gtaagactgg cctggggtaa ccactctatt   5160
tctgggaatt ggaacaagac aagtcagcac atttggactt gaaccttaac ctcattacca   5220
tatcctctcc aaacaagtat tctcggttct attttgtttt tgagcttgtc attttctgca   5280
ctctgaaacc aggtcttctg cttaacttgt atgttgtcaa gtgtttggct gttgacaaaa   5340
taattcaagt aacaattatc attgtggaat tttcattatg tcactggtgg ctcagctggt   5400
aaagaatctg cctgcaatgc aggagacctg ggtttgaccc ctagatcggg aagatcctct   5460
```

-continued ggagaaggaa tgactacccg ctgcagtatt cttgcctgga gaaccccatg gacagaggag 5520
cctggtgggt tacagtgcat ggggttgcaa gagtccgaca tgacttagca actaaactgc 5580
caccaccacg tcaatgggaa atgcagttgt ggcaccgtga ttttcagtgt tcccttactg 5640
catccattgc tgctgctgct aagtcacttc agtcgtgtcc gacggcccac caggctcccc 5700
gtccctggga ttctccaggc aagcacactg gagtgggttg ccatttcctt ctccaatgca 5760
tgaaagtgaa aagtgaaagg gaagtcgctc agtcgtgtcc gactctttgt gaccccatgg 5820
tctgcagcct accaggctcc tccatccatg ggattttcca ggcaagagta ctggagtggg 5880
gtgccgttgc cttctctggc atccattgtt ggggggtagc tattgctttc tctctctcta 5940
agctaggtta tttatggcca taggaattta ggcagggaat aagggaaaaa tggcaactcc 6000
cagggaactt cacccattga gccatatacc acatagttct tagaaactgg attagtccca 6060
ttctaaattc ctgtgggata tttttagttt gaagaaattt ggagggccta gaggcaacag 6120
atagccaata ttcagttttt aatttatgtc tcatcccagt tgttccctgt cactgttcct 6180
gcatatggtg acttttgagt tgactggtat atccttaata ctcattcatt tacagtaatc 6240
agtaatgtgt gtgtgtgttt gcattttgat tttcttttaa aaaattattt acttggctgc 6300
tctggatctt agttgctgca tgtgaactct tagttgccac aggtggggtc tagttccctg 6360
accaggatcg aacccaggcc cctccgttgg gagtgcagag gcttagtcgc tgggatacca 6420
gagaagtcgc ctgcatttgt attttcaaag ggctacttac tttctcaagt taagttaccc 6480
tctaaattaa attatcccat agaattctaa agtgtaaagt tcacagattt tttaggatat 6540
tgcagagggt ggggagggaa ggttgttttt tttttttcc tgttttgttt tgctttttaa 6600
aggaaatttg tgtagtgtag taatgatctg gctaggattc tgtgagtggg ttattttctc 6660
tgttcatgat ttatgcactt tgagaaaatt tggcatctta aggtagggac catgacttct 6720
ccatataaat aaacatcata aaaaggcttg taccttttac tctggtaatt ctcactaaaa 6780
gtgagctgct gatgagaaca ttctatgtgg gtaactactc aggggccaca tgctgttcaa 6840
agcctggtca aggtttacag ttctcttggt atagtaacat atacgattag gcacttagcc 6900
ttttaatgaa gataaatata tgtaacaatt atatttggaa aaatgtaatc atatttgaaa 6960
tattaaaaag ctggctatta gcaattttgg tgtagtctat aaaaagatga atcattgctc 7020
aggataatta gttaaaagct ctcattatga attgttttct ttaaaaagca ttaagatatt 7080
taccatgtac tgtgtgatgg aagattcctc aggtatgctg tgcattgttc atttgtcttt 7140
ctgtgaccgg tatcctagaa tcctgtactc tcttctactt catctccttt tctctttcta 7200
actctggatt gtgcttctgg tattctgctt aaatcattct gggccccggc agtcttccag 7260
ttcaatcaca tggacttacc cagtgtgtca ccctatttct gacacttcac actattgtct 7320
gcctctgtct caccagaatt ccttggcaca ttaacccggt ttcctctcac ccttccaacc 7380
gtcttttcct ctggtccctc ctatcttcgg tcttttgctg ttgtatcccc caaggctctg 7440
tttttgcctc tcttcccatc tttctgagta cttgtgatct ttcagcacag atcatttcaa 7500
ctctctctgc ttttctgtct ctgtgttagt atcgtgttcc tgctgcctaa aggatagatg 7560
tactgccgca gcctcaattc atcccacaga agacagaaca tagcatcatt ttctccacct 7620
ggcacccttc ctactgaatt tctgcctgaa atgaaattct tcttctagtc tccaaaacta 7680
gacacctggg attcatccct gcctcagtga cttttcttcg ccctgtctct tggtttcctc 7740
tgtccttttc ttacctatga acagaccctc cagactttcc ctctgaagca tgacctaccg 7800
gctcagtgtt tcagctcttt acgacccaca ctcccctgat gctgccagcg ctctctgcct 7860

-continued

```
tcgtgattgt ctctaaactg gcagaaccat cactattaca gttggctttt ccacttggtg   7920
atccttgttt ttggaaaatc ctttatcaca ccaattcttg tctcacaccc tcctcccact   7980
ctcacttttc cctgaaaaga tcttttacga gccagctcag tggtcttttc ctttgtgaaa   8040
ctttcccccta ccttcccagg gagacttggt tgtttctgtc tgtgcttttt tccccatagt   8100
agttgggatg gattgtagac ttaacagttt ttcttgtaat taattgttta catgtctatc   8160
tcctgcactg ggactgcgag ctctgtctac ttaaagaatg tgttttaagt tcagtgtgta   8220
cccaacaaat gagccaagtc ttctgactcc ctctctgatg gccttctgac atccttctcc   8280
tcttagcctt gactcaggcc gtttccctga gctgaagtgc acttagtcct ccttcctgac   8340
cccagtccta ggctttgcgt cagaccctgt ggctttcaca tggccctgta cccgtctgtc   8400
ctctcctgcg ttatcgaaaa attctctcta atagcttgat gtgttttaac ctcctgtccc   8460
tcagttttac tggaactttc tagatggcaa ggattttaaa aaatttaaac attacccagt   8520
agtcctttgc tctcttttct actctgagga ctgagactga ctttaggcac tccagaattc   8580
cctggactca aatgaatgac catgctgagg cccatgaaga ggttcgatgt gtattgttga   8640
atgagctaga actttaaata aataagcata tacacttcag catgaagtgc gcagagcaga   8700
taagttgaac gtagcatcac tgtggttcct tctgtggaca cctttcacat tattcaaagg   8760
aagcaataaa ggtaaaacac aatcatttca ttaggattaa tttttattgt ggaagttttt   8820
cttttcagct aatgaataac atgtcaacat ttctagccaa tttcagaact agctgtaatc   8880
ttttaattaa aaaccataga tctgagagtt catacttgag tcatatttaa tccttaaatc   8940
cctttctttc cctctgtctc tttctctctt tctaaaagct gtgaatcatt ttataaatta   9000
ggattaagaa ctgtctggta ccattgttaa tatccctttt ggctgtgagg aaatggcaca   9060
aataatttca tcctaatatt cattcagatt tatgagccag tattcatcac aacaatctta   9120
aaactcttga aaggatagaa actgtatgac aaagtgagtc atagtctttg tgatgtgatg   9180
tctgcaaggg tgggtgggag agactactga atgaccagtc tcattctgct ttctgagctg   9240
aatcattttg caaatagaaa acaattcata gatttataga tggtcataac ataaatagga   9300
aatggaagag agtaacagag tcaaataata cctctattta aaaaattact ttttgaaaca   9360
taacacttga tgaacagtct ttattttgaa ttagaaatga aattaatcta ctgcctaata   9420
atacatatat tttgatactt gctgtatgtc tttatatatt ttcatttttt cctattggtt   9480
atgtttcttt taaaaaattc tctcatgtaa tttgaccttt atcttcatag ctatttctag   9540
ctttggcttg tttgacaatt gcgtgtgtgt ttgtgtgtgg agaaggaggg gactacttgt   9600
atggaaactt gagagaagaa ggtccctttc ctcttgaaaa ttcttaatag tataatcctg   9660
cattttgcat ggtcggtctc cttttgttac ttttcatctt actagaatta gcaatatgga   9720
gagtctttct ctgagtcaga tttaaccttt aatctttaaa tgtaagattg atttacctta   9780
tttccttatt ttctttgaga caaagtattt gtcaaaacaa ttatatgaaa agtaaactat   9840
tctagtttga gtgtgtttct tgagttttag aactttagga ctcttcttac attcttatat   9900
ttatccatta aactcaacaa tttagtaagg gggatataat acaaataaaa ttgggaagct   9960
aatttttcta actggtttag tagaggacag tagtatatga agaagacata tattacattt  10020
aatacaacgt gttggattaa aaaatagtta cagcaatacc ttcagctgtt acaaggtggg  10080
aaaagtaagg cgcagattat tttggaggga aggtattaaa accatgacgt gttgatggga  10140
tctgtccagc ctgagccaga caccaaagca ggttccatgg caacttggcc acgtccctgc  10200
```

-continued gcctttaaag aggaagggcc tattgtttgg ccttcaccaa atgacttcac ctgggatctt 10260
gttatttact gaatgttttt tgaatggatg gatgaaattc ctgagaacat gctctgggcc 10320
agctttatga acagtatgtt taatcttatt gtagtcttat gaaagaagtg ttattttcat 10380
cttacagata gggatagagt ttttgctatt ggcttttcaa accatggtct ctttgtgatt 10440
gtaagtaatt aattgtgtct tccagatttg ttagtgttta gaatacagtt catggccaga 10500
atttcagatg gacggtgtgg cataaatttg aacagaaata gtgattttta aaaatagttt 10560
aaacttccca gagcctttac tgtgctcagc aaagttagtc tctcatcttt tcttctaccc 10620
ctttattgca tcctttttta tttagaaaat atttgtcatg aattaatacg aaacaattct 10680
ttaatatttt agggattgct ttctgaagaa ctcaaagatt tttaaaaggc atatttaaaa 10740
attaagagca ggacataatt aagaataaat accatataag aatgggataa acctcaaaga 10800
tagagtctgt aaagatgcag aataagctaa ggcatgcaga aaatacaaag agaatgatta 10860
aaaggatgtt taaaaagtta gttaggccct ttcaaggaaa tttgagatag gctcactatt 10920
taaggacata gtgtaagatg aaaagaaaaa aatttagaaa aaaaagcaga tggacctggg 10980
cctattttat gttaatgtta atcttcttct ccaagtgaga ttgtcaatca ataattgtct 11040
gagtgtctca ttgagaaaat aaagaccaag gtagacaaag agatacaaag aaagcactta 11100
gccagacaca tctagaaatg tgtttataat gaaactcctc tttccttgaa atcacttgtc 11160 ccccttttttt gaccccctgt attttaaaat ataaaatatt taactttgta aatttcttgc 11220
caaccagccc atctcgcaga gtacatttct actcttcatc ccctcagtct tcacatccgt 11280
ctcaggctct gtgttttcag ttctgctgtg tccttcatac tcacgggggt ctctgcattg 11340
ttgccacagc tgctctcgtt cggtccctga ctgttgcaac tgccttctac ctgatcccat 11400
ctgtatcagt ttgctagggc tgccataaca gattaccgta gactgagtgg ctcaaacaac 11460
agaaattgat tttctcatag ttctgtagac tagaagtcca agatacagct gtctgcatgt 11520
ctggtctttc tgcggcctct tcggggtttg cagcagccac cttacacatg gtcacctctc 11580
tgtgcacaca tcctgatctc ttcttcttgt aagggcacca ttcagatttg gttagggccc 11640
actctrtaac agccccattt tgacttaatc cttctttaga ggccccatct ccaaatagta 11700
attttctgag gtactggggc ttcaggcttc agtgtatgaa tttggggtgg gggtacagtt 11760
cagcccacag caccagtgag tcaactggat attgttcctt ggcagagtat ctttccagag 11820
agcagctctg atcttgttat ccctctattt agaaaaactt catggacagt ctagtcccct 11880
ggttcccaca ttgcttacag atgtgggcac tgtagaaagt ctatgagaat tacagagaat 11940
aggaagttac cagcagatga gtgattgtct tatatatcag aaagtgggat aaaggtattt 12000
tctggaaact ctagatagct aggaagcctg atgtaggtcc ttgaaaaaaa tccaagggac 12060
ttgagaatac ggagaaaaga agataacata gaaaatagta aataggctcg 12110

<210> SEQ ID NO 7
<211> LENGTH: 1620
<212> TYPE: DNA
<213> ORGANISM: Bos taurus
<220> FEATURE:
<221> NAME/KEY: misc_feature
<222> LOCATION: (975)..(975)
<223> OTHER INFORMATION: s is c or g

<400> SEQUENCE: 7
ggctcagcgt ccctcccctc ccgcaggggc agtgacaccc tgagctgtcc tggggaccct 60
gagggaggca gagagccagg aggagagcgg gacccagcag agcaggaggc ccgggccttc 120

```
ttcctcatgg ggcctgaggg ggagagtcgg tctgggagga ggaggccctg cagggctgtt    180

ctgagagccc agaagggccg gctgagccac cgcccgaccc tcaggagctg gccgagaagc    240

accagaagac cctgcagctg ctgcggaagc agcagaccat catcctggat gacgagctga    300

tccagtggaa gcggcggcag cagctggcgg ggaacggagg gccccccgag ggcagcctgg    360

atgtgctaca gtcctggtac caggggtggg gggcggggag gggcaggcag cagagtggtg    420

ctgccagctg ctgtttgcgc ccacgtctac atgagcagct ggctccctct gtctgggcgc    480

gggtcttatc ccaccagtgg tgtgtttggt gctgacaccg gtgtcccttt ctgtgccccc    540

tcccctggga ggatgctggg gtggggccag gtggcaaagt ggcgctcagg ctggttggac    600

cccagtcagt gtcgctcctc ctgggtgttt ctctggtttt tttggaaggc agggcatctc    660

tgctgtgccc agtgcacagg cgaggtggct cgggcaccag gccttcctgg gggtggagct    720

gggtgtgggc cttgtccccg cctgggcgcc tgccagcttc tggcctggag gacgggggtg    780

aagcccgtgt ccttcccttg ggccctgggg ctcgggttca ggtgtgagaa gttggcggag    840

attatctggc agaaccggca gcagatccgc agagccgagc acctctgcca gcagctgccc    900

atccccggcc ccgtggagga gatgctggct gaggtcaacg ccaccatcac tgacatcatc    960

tcagccctgg tgacsaggtg actcctggcc acgccccgct cccatctggt tgccctgggt   1020

tgggggcagc agggtctttg cagatgggga gctctggctt aaatccttca gtttctgcct   1080

cacaccctcc tcccatccct ctccatcccc tgttgctatg gcctcttgct gtcgacctca   1140

cccagtattt ctcgtggaca ctacacgggc atttgtctcc tgcaactcct ttcagctgct   1200

gagttccttt tactgcctcc cttcccgcca gctcccctga ctcacagtgg ccccagggag   1260

ggtggactgt ccgcaaaccc tcccttcacc tgctcagcct ggtgcaaggc agcctcccca   1320

cgtggaaggt ggggccagag tcctgtcccc tgaagtgtct cctgtccctt gtgtctccgc   1380

agcaccttca tcatcgagaa gcagcccccct caggtcctga agacccagac caagttcgcg   1440

gccaccgtgc gcctgctggt gggtgggaag ctgaacgtgc acatgaaccc cccccaggtg   1500

aaggccacca tcatcagcga gcagcaggcc aagtcactgc tcaagaacga gaacacccgc   1560

aagtatgctg cccgctcctt catctgccct cccccagctc agcctctgct ctgtagctgg   1620
```

<210> SEQ ID NO 8
<211> LENGTH: 32
<212> TYPE: DNA
<213> ORGANISM: artificial sequence
<220> FEATURE:
<223> OTHER INFORMATION: primer GHR-F

<400> SEQUENCE: 8

```
ctttggaata cttgggctag cagtgacaat at                                 32
```

<210> SEQ ID NO 9
<211> LENGTH: 20
<212> TYPE: DNA
<213> ORGANISM: artificial sequence
<220> FEATURE:
<223> OTHER INFORMATION: primer GHR-R

<400> SEQUENCE: 9

```
gtctctctgt ggacacaaca                                               20
```